(12) United States Patent
Cao et al.

(10) Patent No.: US 10,213,107 B2
(45) Date of Patent: Feb. 26, 2019

(54) METHODS AND DEVICES FOR IMPLANTATION OF INTRAOCULAR PRESSURE SENSORS

(71) Applicants: Ariel Cao, Oakland, CA (US); Enrique Malaret, Shorewood, MN (US)

(72) Inventors: Ariel Cao, Oakland, CA (US); Enrique Malaret, Shorewood, MN (US)

(73) Assignee: Injectsense, Inc., Emeryville, CA (US)

( * ) Notice: Subject to any disclaimer, the term of this patent is extended or adjusted under 35 U.S.C. 154(b) by 673 days.

(21) Appl. No.: 14/789,491

(22) Filed: Jul. 1, 2015

(65) Prior Publication Data

US 2016/0000325 A1 Jan. 7, 2016

Related U.S. Application Data

(60) Provisional application No. 62/019,826, filed on Jul. 1, 2014.

(51) Int. Cl.
*A61B 3/16* (2006.01)
*A61B 17/34* (2006.01)
(Continued)

(52) U.S. Cl.
CPC ............ *A61B 3/16* (2013.01); *A61B 17/3468* (2013.01); *A61B 2090/064* (2016.02); *A61F 9/00781* (2013.01)

(58) Field of Classification Search
CPC .... A61B 3/16; A61B 17/3468; A61F 9/00781
See application file for complete search history.

(56) References Cited

U.S. PATENT DOCUMENTS 5,178,635 A * 1/1993 Gwon ................ A61F 9/0017
  250/302
5,626,559 A    5/1997 Solomon et al.
(Continued)

FOREIGN PATENT DOCUMENTS

CA   2904642    10/2014
CN   103190983   7/2013
(Continued)

OTHER PUBLICATIONS

Hague, R.M. et al., "A 3D Implantable Microsystem for Intraocular Pressure Monitoring Using a Glass-In-Silicon Reflow Process," Micro Electro Mechanical Systems (MEMS), Jan. 23-27, 2011, IEEE 24th International Conference, pp. 995-998.
(Continued)

*Primary Examiner* — Daniel Cerioni
*Assistant Examiner* — Nicholas E Kolderman
(74) *Attorney, Agent, or Firm* — Kilpatrick Townsend & Stockton LLLP

(57) ABSTRACT

Methods and devices for implanting an intra-ocular pressure sensor within an eye of a patient are provided herein. Methods include penetrating a conjunctiva and sclera with a distal tip of a fluid-filled syringe and positioning the pressure sensor within a vitreous body of the eye by injecting the sensor device through the distal tip. The sensor device may be stabilized by one or more anchoring members engaged with the sclera so that the pressure sensor of the sensor device remains within the vitreous body. Methods further include advancing a sensor device having a distal penetrating tip through at least a portion of the sclera to position the sensor within the vitreous body and extracting of the sensor devices described herein by proximally retracting the sensor device using an extraction feature of the sensor device.

30 Claims, 19 Drawing Sheets

(51) Int. Cl.
*A61F 9/007* (2006.01)
*A61B 90/00* (2016.01)

(56) References Cited

U.S. PATENT DOCUMENTS

| | | | |
|---|---|---|---|
| 5,868,697 A * | 2/1999 | Richter | A61F 9/0017 604/294 |
| 6,186,974 B1 | 2/2001 | Allan et al. | |
| 6,346,742 B1 | 2/2002 | Nasiri et al. | |
| 6,666,841 B2 | 12/2003 | Gharib et al. | |
| 6,736,791 B1 | 5/2004 | Bergheim et al. | |
| 6,936,053 B1 | 8/2005 | Weiss | |
| 6,979,872 B2 | 12/2005 | Borwick, III et al. | |
| 6,981,958 B1 | 1/2006 | Gharib et al. | |
| 7,135,009 B2 | 11/2006 | Tu et al. | |
| 7,149,587 B2 | 12/2006 | Wardle et al. | |
| 7,163,543 B2 | 1/2007 | Smedley et al. | |
| 7,186,232 B1 | 3/2007 | Smedley et al. | |
| 7,431,710 B2 | 10/2008 | Niksch et al. | |
| 7,488,303 B1 | 2/2009 | Haffner et al. | |
| 7,509,169 B2 | 3/2009 | Eigler et al. | |
| 7,563,241 B2 | 7/2009 | Tu et al. | |
| 7,678,065 B2 | 3/2010 | Haffner et al. | |
| 7,708,711 B2 | 5/2010 | Gharib et al. | |
| 7,732,302 B2 | 6/2010 | Yazdi | |
| 7,819,014 B1 | 10/2010 | Broden | |
| 7,850,637 B2 | 12/2010 | Lynch et al. | |
| 7,867,186 B2 | 1/2011 | Smedley et al. | |
| 7,900,518 B2 | 3/2011 | Tai et al. | |
| 7,951,155 B2 | 5/2011 | Burns et al. | |
| 8,118,768 B2 | 2/2012 | Tu et al. | |
| 8,142,364 B2 | 3/2012 | Haffner et al. | |
| 8,303,511 B2 | 11/2012 | Whiting et al. | |
| 8,322,346 B2 | 12/2012 | Najafi et al. | |
| 8,336,387 B2 | 12/2012 | Tai et al. | |
| 8,337,445 B2 | 12/2012 | Niksch et al. | |
| 8,475,374 B2 | 7/2013 | Irazoqui et al. | |
| 8,478,415 B1 | 7/2013 | Halla et al. | |
| 8,506,515 B2 | 8/2013 | Burns et al. | |
| 8,549,925 B2 | 10/2013 | Tai et al. | |
| 8,585,630 B2 | 11/2013 | Meng et al. | |
| 9,022,968 B2 | 5/2015 | Passaglia | |
| 9,173,564 B2 | 11/2015 | Choo et al. | |
| 9,301,875 B2 | 4/2016 | Niksch et al. | |
| 9,314,375 B1 | 4/2016 | Passaglia | |
| 2003/0060752 A1 | 3/2003 | Bergheim et al. | |
| 2003/0060763 A1 | 3/2003 | Penfold et al. | |
| 2003/0078487 A1 | 4/2003 | Jeffries et al. | |
| 2004/0050392 A1* | 3/2004 | Tu | A61F 9/00781 128/898 |
| 2004/0073137 A1* | 4/2004 | Lloyd | A61B 3/16 600/561 |
| 2004/0104754 A1 | 6/2004 | Bruchhaus et al. | |
| 2004/0116524 A1 | 6/2004 | Cohen et al. | |
| 2004/0215133 A1* | 10/2004 | Weber | A61F 9/0017 604/60 |
| 2005/0019371 A1* | 1/2005 | Anderson | A61K 9/0051 424/426 |
| 2005/0196424 A1* | 9/2005 | Chappa | A61K 9/0051 424/423 |
| 2005/0288604 A1 | 12/2005 | Eigler et al. | |
| 2005/0288722 A1* | 12/2005 | Eigler | A61B 5/0215 607/9 |
| 2007/0156079 A1 | 7/2007 | Brown et al. | |
| 2008/0057106 A1 | 3/2008 | Erickson et al. | |
| 2008/0097335 A1* | 4/2008 | Trogden | A61F 9/0017 604/192 |
| 2008/0161741 A1 | 7/2008 | Bene et al. | |
| 2010/0016704 A1 | 1/2010 | Naber et al. | |
| 2010/0152646 A1 | 6/2010 | Girijavallabhan et al. | |
| 2010/0280349 A1 | 11/2010 | Dacquay et al. | |
| 2011/0082385 A1 | 4/2011 | Diaz et al. | |
| 2011/0301434 A1 | 12/2011 | Haque et al. | |
| 2012/0004528 A1 | 1/2012 | Li et al. | |
| 2012/0078362 A1 | 3/2012 | Haffner et al. | |
| 2012/0165933 A1 | 6/2012 | Haffner et al. | |
| 2012/0197101 A1 | 8/2012 | Telandro | |
| 2012/0197155 A1 | 8/2012 | Mattes et al. | |
| 2012/0209100 A1 | 8/2012 | De Beeck et al. | |
| 2012/0226132 A1* | 9/2012 | Wong | A61B 3/16 600/398 |
| 2012/0226133 A1 | 9/2012 | Wong et al. | |
| 2012/0253258 A1 | 10/2012 | Tu et al. | |
| 2012/0259195 A1 | 10/2012 | Haffner et al. | |
| 2012/0302861 A1 | 11/2012 | Marshall et al. | |
| 2013/0009053 A1 | 1/2013 | Wu | |
| 2013/0018440 A1 | 1/2013 | Chow et al. | |
| 2013/0036827 A1 | 2/2013 | Besling | |
| 2013/0090534 A1 | 4/2013 | Burns et al. | |
| 2013/0184554 A1 | 7/2013 | Elsheikh et al. | |
| 2013/0298699 A1 | 11/2013 | Potasek | |
| 2013/0324942 A1* | 12/2013 | de Juan, Jr. | A61F 9/0017 604/246 |
| 2014/0012177 A1 | 1/2014 | Tu et al. | |
| 2014/0016097 A1 | 1/2014 | Leonardi et al. | |
| 2014/0039456 A1* | 2/2014 | Lerner | A61M 5/427 604/506 |
| 2014/0088400 A1 | 3/2014 | Irazoqui et al. | |
| 2014/0275923 A1* | 9/2014 | Haffner | A61B 5/6867 600/377 |
| 2014/0303544 A1 | 10/2014 | Haffner et al. | |
| 2016/0015265 A1 | 1/2016 | Mandel et al. | |
| 2016/0015266 A1 | 1/2016 | Kim et al. | |
| 2016/0064867 A1 | 3/2016 | Bergner | |
| 2017/0251921 A1 | 9/2017 | Truong et al. | |

FOREIGN PATENT DOCUMENTS

| | | |
|---|---|---|
| WO | 2009129450 | 10/2009 |
| WO | 2011035262 | 3/2011 |
| WO | 2013040079 | 3/2013 |
| WO | 2013056130 | 4/2013 |

OTHER PUBLICATIONS

Hague, R.M. et al., "Hermetic Packaging of Resonators With Vertical Feedthroughs Using a Glass-In-Silicon Reflow Process," Solid-State Sensors, Actuators and Microsystems 16th International IEEE Conference, Transducers, Jun. 5-9, 2011, pp. 2303-2306.

Wang, Fei et al., "Electrostatic Energy Harvesting Device With Out-Of-The-Plane Gap Closing Scheme," Sensors and Actuators A: Physical, Jan. 2014, 4 pages.

International Search Report and Written Opinion dated Oct. 6, 2015, from International Application No. PCT/US2015/038902 (12 pages).

Invitation to Pay Additional Fees and Partial Search Report dated Sep. 4, 2015, from International Application No. PCT/US2015/038917 (2 pages).

Invitation to Pay Additional Fees and Partial Search Report dated Sep. 10, 2015, from International Application No. PCT/US2015/038862 (2 pages).

Unpublished U.S. Appl. No. 14/789,839, filed Jul. 1, 2015, to Ariel Cao, titled Hermetically Sealed Implant Sensors With Vertical Stacking Architecture.

Unpublished U.S. Appl. No. 14/789,942, filed Jul. 1, 2015, to Ariel Cao et al., titled Ultra Low Power Charging Implant Sensors With Wireless Interface for Patient Monitoring.

"Auto Regulation System for Intraocular Pressure", USF Available Technologies, Technology Transfer Office http:/ /www.usf.edu/research-innovation/pl/, 1 page.

"MEMS Intraocular Pressure Sensor", SBIR.gov, https://www.sbir.gov/sbirsearch/detail/214217, 2 pages.

"Nanophotonics-Based Implantable Iop-Sensor With Remote Optical Readout", https://techtransfer.universityofcalifornia.edu/NCD/24177.html, 5 pages.

"Optical-Based Intraocular Pressure Sensor", Research Affairs, Office of Innovation and Commercialization, US San Diego, https://techtransfer.universityofcalifornia.edu/NCD/24855.html, 5 pages.

"The Choo Lab", Division of Engineering and Applied Science, httpiieas.caltech.edu, http:/ l choo lab. caltech. edu/research.html, 4 pages.

(56) References Cited

OTHER PUBLICATIONS

Acumems Inc., "AcuMEMS Announces New Glaucoma Product for Cataract Surgery", AcuMEMS Announces New Glaucoma Product for Cataract Surgery, Business Wire. http://www.businesswire.com/news/home/20101015005202/en/AcuMEMS-Announces-New-Glaucoma-Product-Cataract-Surgery, Oct. 15, 2010, 2 pages.

Araci et al., "An implantable microfluidic device for selfmonitoring of intraocular pressure", Nature Medicine 20, 2014, pp. 1074-1078.

Bhamra, "Implantable Ultra-Miniature IntraOcular Pressure Sensor", CID Home, Implantable Ultra-Miniature Intra-Ocular Pressure Sensor—Center for Implantable Devices, https:/1 engineering. purdue. edu/CID /implantable-ocular-pressure-sensor .html, 2 pages.

Caceres, "Nanophotonics-based implant may enable at-home IOP monitoring", OphthalmologyTimesOphthalmologvCalit{)rnia Institute of Technology, http://ophthalmologytimes.modernmedicine.com/ ophthalmologytimes/content/tags/califomia, Jul. 15, 2014, 3 pages.

Goldberg et al., "Glaucoma Forum Shedding Light on 'Silent Thief of Sight'", Glaucoma Research Foundation, https://www.glaucoma.org/research/glaucoma-forum-shedding-light-on-silent-thief-of-sight, Feb. 11, 2014, 4 pages.

Kim et al., "Performance of implantable inductive pressure sensor for continuous monitoring of intraocular pressure", ARVO Annual Meeting Abstract, Investigative Ophthalmology & Visual Science vol. 55, 121. doi: http://iovs. arvoj ournals. org/ article.aspx?articleid= 22664 3 7, Apr. 2014, 3 pages.

Kim et al., "Preliminary study on implantable inductive-type sensor for continuous monitoring of intraocular pressure", Clinical & Experirnenta! Ophthalmology, vol. 43, Issue 9, Dec. 2015, pp. 830-837.

Launch Point Technologies Inc., "Intraocular Pressure Sensor: LaunchPoint Technologies", Launch Point Technologies, http://www.launchpnt.com/portfolio/biomedical/intraocular-pressure-sensor, 3 pages.

Lee et al., "Nanoarray-Enhanced Micro mechanical Pressure Sensor with Remote Optical Readout", Advanced Photonics, paper SeTh2D.3, 2014, 2 pages.

Lin et al., "High Quality Factor Parylene-Based Intraocular Pressure Sensor", 2012 7th IEEE International Conference on Nano/Micro Engineered and Molecular Systems (NEMS), 2012, pp. 137-140.

Liu et al., "Estimation of 2~-Hour Intraocular Pressure Peak Timing and Variation Using a Contact Lens Sensor", PLoS One. vol. 10(6), e0129529, Jun. 15, 2015, pp. 1-11.

Ma, "Sensor in eye could track pressure changes, monitor for glaucoma", UW News, Engineering, Health and Medicine, New Releases, Research, Science, Technology http :l !www. washington. edu/news/20 14/06/16/sensor-in-eye-could-track-pressure-changes-monitor-for-glaucoma, Jun. 16, 2014, 5 pages.

Quake, "Eye implant could lead to better glaucoma treatment", News Center, Stanford Medicine http://med.stanford.edu/news/all-news/20 14/08/eye-implant-could-lead-to-better-glaucoma-treatment, Aug. 25, 2014, 3 pages.

Thieme, "New chances for glau om a patients", glaucoma treatment—EYEMATE, Your intraocular pressure look-out, http://www.my-eyemate.com/en/, 4 pages.

* cited by examiner

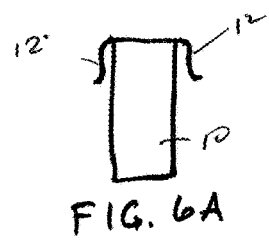
FIG. 6A
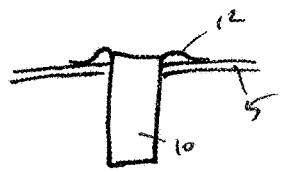
FIG. 6B
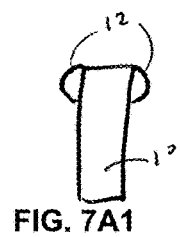
FIG. 7A1
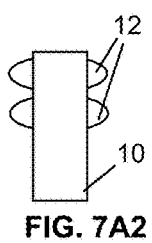
FIG. 7A2
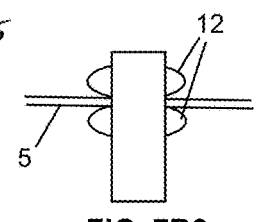
FIG. 7B1
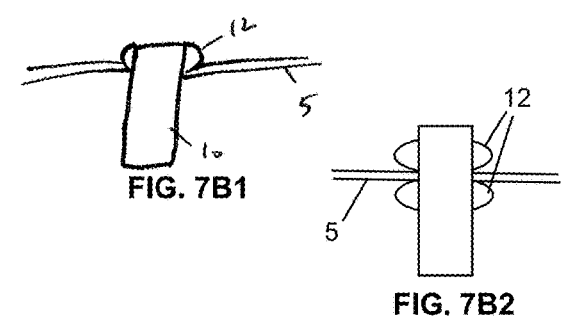
FIG. 7B2
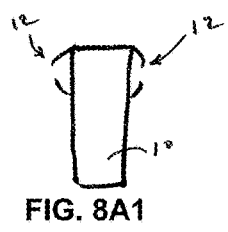
FIG. 8A1
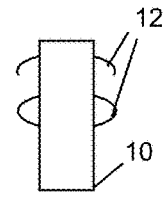
FIG. 8A2
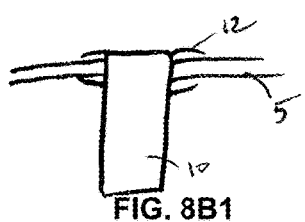
FIG. 8B1
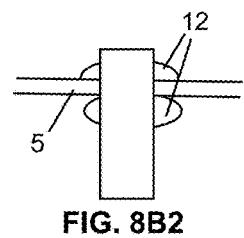
FIG. 8B2
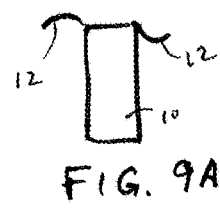
FIG. 9A
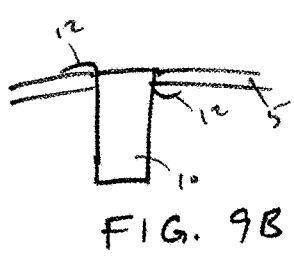
FIG. 9B

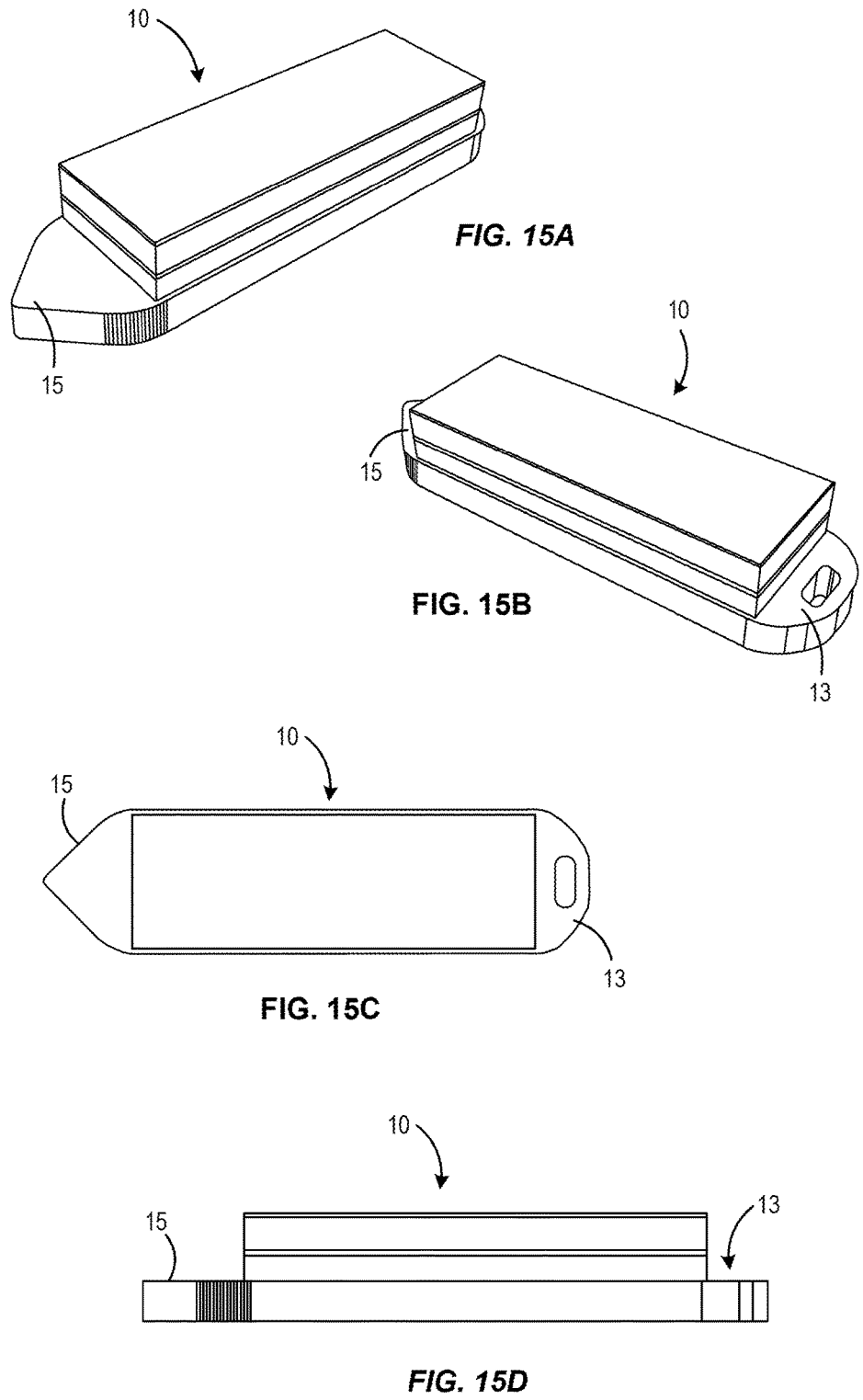

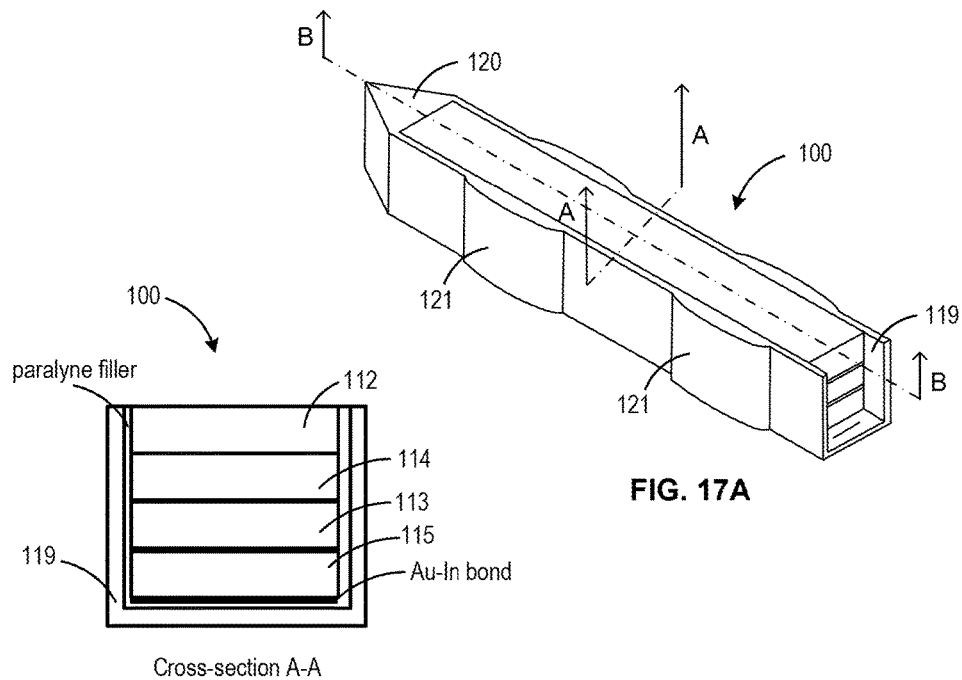
FIG. 17A
FIG. 17B
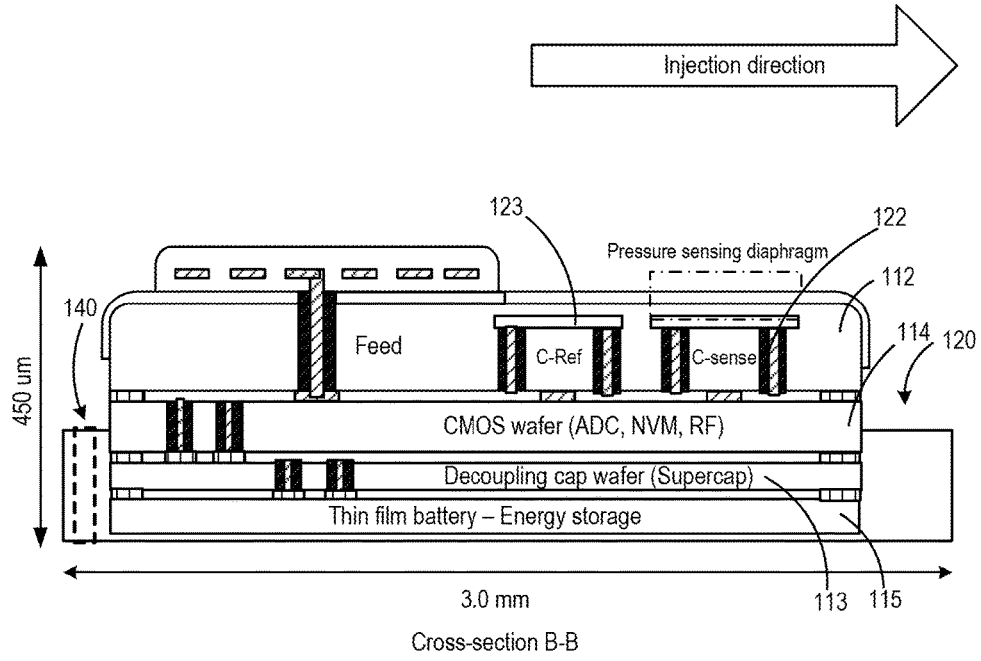
FIG. 17C

METHODS AND DEVICES FOR IMPLANTATION OF INTRAOCULAR PRESSURE SENSORS

CROSS-REFERENCES TO RELATED APPLICATIONS

The present application is a Non-Provisional of and claims the benefit of priority of U.S. Provisional Application No. 62/019,826 filed on Jul. 1, 2014, the entire contents of which are incorporated herein by reference.

The present application is related to co-assigned and concurrently filed U.S. Non-Provisional patent application Ser. No. 14/789,839, entitled "Hermetically Sealed Implant Sensors with Vertical Stacking Architecture"; and U.S. Non-Provisional patent application Ser. No. 14/789,942, entitled "Ultra Low Power Charging Implant Sensors With Wireless Interface for Patient Monitoring"; each of which is incorporated herein by reference in its entirety for all purposes.

BACKGROUND OF THE INVENTION

This application relates generally to devices and methods for implanting an intraocular pressure (IOP) sensor within an eye of a patient, particularly by injecting the IOP sensor device within a patient's eye for monitoring and management of glaucoma treatment.

Glaucoma is a condition resulting in increased pressure within the eye that eventually leads to damage of the optic nerve that transmits images to the brain, which results in gradual vision loss. The increased pressure within the eye causes a loss of retinal ganglion cells in a characteristic pattern of optic neuropathy. A patient suffering from glaucoma typically experiences a build-up of aqueous fluid which increases the pressure inside the eye (i.e. intraocular pressure). Elevated IOP is one of the primary risk factors for developing glaucoma, which must be carefully monitored and controlled in treating glaucoma. As retinal ganglion cells are damaged by glaucoma, the visual signals from at least a portion of visual field are no longer reported to the brain, forming blind spots or scotomas. As glaucoma progresses and increasingly damages more nerve tissue in the optic nerve, vision loss continues as the scotomas increase in size and/or number. Failure to properly treat glaucoma and to reduce and monitor the IOP may cause irreversible vision loss. Untreated glaucoma, which affects one in 200 people under the age of fifty and 10% of those over the age of 80, is the second leading cause of blindness worldwide. As of 2012, about 60 million people suffer from glaucoma world-wide and it is estimated that, by 2020, about 80 million people will suffer from glaucoma. In addition, since a high percentage of people are over the age of 75 years old, and as the world-population ages and life-spans increase, it is expected that glaucoma patient populations will continue to increase.

IOP in a healthy human eye is generally between 10 mmHg and 20 mmHg. Glaucoma causes substantial increase in and/or variation in IOP than that experienced in a healthy eye. The IOP is determined largely by the amount of aqueous fluid entering and exiting the eye. Aqueous fluid is produced by the ciliary body to supply the lens and cornea with nutrients and carry away waste products. Normally, aqueous fluid flows between the iris and the lens, through the pupil and to the drainage angle before exiting the eye through a tissue called the trabecular meshwork in the drainage angle, including the schlemm's canal. If the aqueous fluid is produced at a rate faster than it drains, then the intraocular pressure will rise. An elevated intraocular pressure is associated with two major types of glaucoma: open-angle glaucoma and closed-angle glaucoma. In open-angle glaucoma, the drainage angle between the cornea and the iris is open and allows the aqueous fluid of the eye to reach the trabecular meshwork, but abnormalities in the trabecular meshwork reduce the outflow of aqueous fluid from the eye. In closed-angle glaucoma, obstructions within the trabecular meshwork prevent the aqueous fluid from draining properly out of the eye.

While the progression of glaucoma can be substantially halted in many patients using a variety of treatments, for example, medicines, prescription eye drops, shunts, and surgical procedures, failure to properly diagnose and/or monitor the IOP of a patient can drastically reduce the effectiveness of available treatments. Currently, glaucoma monitoring often uses infrequent IOP measurements obtained by a physician at a medical facility. For example, a typical patient may have their IOP measured on average four to six times per year by non-invasive techniques, such as tonometry. While tonometry techniques are generally low cost, easy, and non-invasive, a number of different types of errors can significantly reduce the accuracy of this diagnostic tool and as such potentially result in inappropriate diagnosis and/or ineffective follow-up medical treatment.

For example, at least some of these non-invasive clinical techniques may not detect elevated IOP levels (e.g., pressure spikes) as only a single point measurement is taken during an eye exam. Failure to continuously and/or frequently monitor IOP levels outside the eye clinic (e.g., more than four to six measurements per year) may lead to inaccurate detection of the patient's real IOP profile (e.g., real IOP may be higher or lower than measured IOP). Non-invasive measurements in some instances lack accuracy as these devices measure pressure of the eye with an external sensor that provides an indirect measurement of the actual pressure inside the eye and are unable to capture the dynamic state of the disease in which there is a continuously changing IOP at low and high frequency rates with up to 12,000 spikes per hour. For example, factors that affect accuracy may include failure to account for anatomical differences, such as a patient's cornea thickness, scleral rigidity, or conical curvature, variances due to operator's use or technique, physiological influences, such as caffeine or alcohol use, or prior refractive surgery that may affect a patient's IOP, etc. Hence, the indirect IOP measurements from such non-invasive devices may differ from the actual IOP inside the eye (e.g., overestimated or underestimated) which may lead to inappropriate diagnosis and/or follow-up treatment. Further, it is often inconvenient and impractical for patients to visit the eye clinic on a strict regular schedule for repeated IOP measurements.

Although implantable IOP devices have been proposed for direct IOP measurements on a daily basis, these first generation implants may also suffer from several drawbacks which in turn may result in indirect and/or inaccurate measurement of IOP and inappropriate medical treatment of glaucoma. For example, the IOP devices may be too large or bulky in dimension, size or shape to be safely and effectively placed entirely within a desired location or structure of the eye for direct measurement of IOP. Further, some devices may be extremely invasive, requiring major surgery for implantation and/or complicated positioning of multiple components which are each implanted in different structures or areas of the eye, which unnecessarily increases patient risk and/or injury and total healthcare costs.

Further, some IOP implantable devices may utilize pressure ports which are susceptible to sensing inaccuracies or require direct implantation within certain anatomical locations, such as the anterior chamber, posterior chamber, suprachoroidal space, or cornea of the eye which may lead to unanticipated complications. Also, some of these devices may not be well suited for chronic implantation due to IOP implant design issues of water ingress and/or thermal stress (e.g., associated with polymer packaging), which in turn precludes continuous monitoring of IOP. Such proposed flexible sensors also have issued of degraded stability. In some instances, some IOP devices also suffer from poor calibration and/or monitoring is not adjustable so as to further result in inaccurate IOP detection levels.

Accordingly, it would be desirable to provide improved implant devices and methods of implantation that overcome at least some the above mentioned shortcomings. In particular, it would be desirable to develop ultra-miniature implantable IOP devices that accurately, continuously, and adjustably monitor IOP levels. Ideally, such devices should directly measure IOP pressure levels and can be safely and effectively implanted entirely within a desired location within the eye quickly and easily in an outpatient environment, such as the physician's office, without invasive major surgery. Such devices should further allow for chronic implantation so as to provide long-term stable and continuous IOP measurement profiles for appropriate diagnosis and follow-up therapy. In addition, there exists a need for improved methods of implantation for such devices within the eye that do not require surgical intervention and avoid damage to the sensitive structures of the eye.

BRIEF SUMMARY OF THE INVENTION

The invention provides devices and methods for implanting an IOP sensor within the eye of a patient. In one aspect, such methods include injecting a sensor device within the eye to provide improved sensing and/or monitoring of IOP for use in glaucoma treatments.

Since the mechanisms contributing to the increase in intra-ocular pressure occur within the anterior chamber or adjacent thereto, conventional methods generally focus on measuring intraocular pressure within the anterior chamber. Because the anterior chamber is a particularly sensitive region, great care must be taken to avoid contacting the various parts of the anterior chambers, which may result in damage to the delicate structures therein and degrade visual function. In one aspect, the present invention relates to measuring IOP of the eye by measuring pressure within the vitreous body. Since the pressure within the anterior chamber pushes against and increases the pressure within the vitreous body, measurement of pressure within the vitreous body provides a relatively accurate pressure measurement of IOP of the eye. In certain aspects, the methods of measuring IOP include positioning a pressure sensor within the vitreous body such that the entire pressure-sensing membrane of the pressure sensor is maintained within the vitreous body. In one aspect, the IOP measurement of pressure within the vitreous body may be compared to and correlated with a pressure within the anterior chamber, which may be measured according to various other independent measurement methods. This comparison or correlation can determine any degradation or attenuation of the intraocular pressure, if any, as it is transmitted from the anterior chamber to the vitreous body. Studies suggest that pressure between the anterior and posterior chamber may equalize such that a change in pressure in the anterior chamber will be reflected in the posterior chamber with a slight time delay. Monitoring the anterior chambers directly is not worth the risk of affecting vision significantly or the associated liability. Even if there were a slight degradation or attenuation in IOP when measuring within the vitreous humour, the increased pressure may be detected with a continuous pressure profile that will satisfactorily quantify the increase in pressure in the anterior chamber. The proposed measurement locations can be readily validated across a range of animal models, which may also be used to adjust the sensor sensitivity if necessary. The actual pressure of interest is the pressure seen by the optical nerve head (ONH) which is the pressure that, if excessive, leads to apoptosis or death of retinal ganglion cells and axons.

In certain aspects, methods of implanting an IOP sensor within the eye include penetrating a distal tip of an injector or syringe through a conjunctiva and a sclera of the eye into the vitreous body and injecting the IOP sensor through the distal tip of the injector or syringe. Positioning the IOP sensor may include distally advancing the distal tip of the injector or syringe until a distal facing surface of the injector or syringe abuts against the conjunctiva. In some embodiments, the sensor device has a maximum thickness and width of about 600 microns or less to facilitate injection through a needle having a gauge of 19 or higher (e.g. 28 or 29 gauge) along an insertion axis in-plane with the sensor device.

In embodiments in which the sensor device is injected with a fluid filled syringe, methods may include positioning the injector or syringe within or near an ora serrata region of the eye, for example the pars plana region in between the ora serrata and limbus, prior to penetrating the distal tip of the injector or syringe so as to avoid any optic structures of a retina of the eye. In some embodiments, the syringe may be positioned along the pars planar. In some embodiments, a fluid is injected into the conjunctiva prior to penetrating the distal tip of the injector or syringe, thereby creating a ballooned portion of the conjunctiva in the ora serrata region. The fluid may include an anesthetic to reduce sensitivity in the eye of the patient prior to penetrating the sclera with the distal tip of the injector or syringe. Typically, the distal tip of the injector or syringe is then offset by a small distance, such as about 2 mm or less, before penetrating the sclera. The ballooned portion facilitates deployment of the anchor along the sclera and covering of a proximal end of the device with the conjunctiva after implantation. Methods may further include releasing the IOP sensor from the syringe by displacing a fluid within the syringe. This release may be effected by proximally retracting the distal tip into the syringe. This approach allows the user to stabilize a position of the IOP sensor within the vitreous body during release from the syringe.

In some embodiments, methods of implantation include penetrating partly through a sclera of the eye with an instrument and advancing the IOP sensor into the partly penetrated sclera so as to complete penetration of the sclera with a distal tip of the IOP sensor. In some embodiments, this allows the release of the IOP sensor without penetrating the distal tip of a needle of the syringe through the sclera. For example, the distal tip may be inserted only partly into the sclera before advancement of the IOP sensor causes the IOP sensor device to penetrate through the remainder of the sclera and into the vitreous body. Such embodiments may include a distally tapered tip on the sensor device of sufficient strength and stiffness to penetrate through the sclera or at least a portion thereof. In some embodiment, the distal penetrating tip may be formed within a same layer or substrate as the one or more anchoring members formed at a proximal end of the sensor device. In other embodiments, the distal penetrating tip may be included within an outer casing, housing or "boat" structure that extends at least partly about the IOP sensor device.

In another aspect, methods of implantation further include anchoring of the sensor device within the eye by deploying one or more anchoring members against the sclera. The one or more anchoring members may be defined so as to be resiliently biased to extend laterally outward relative to the insertion axis. The outwardly extending anchors may be sufficiently flexible to be bent toward the insertion axis and constrained within the distal tip of the syringe when injected. Upon release from the distal tip of the syringe, the anchoring members are deployed proximally of the sclera so as to engage an outer surface of the sclera to inhibit movement of the IOP sensor further into the cortical vitreous body vitreous body at the periphery of the posterior chamber and away from retina and ciliary body.

In one aspect, the one or more anchoring members and the IOP sensor are defined portions of a wafer or substrate of the sensor device. At least a portion of the IOP sensor may include a MEMs device formed by a wafer process. In such embodiments, anchoring may include engaging the sclera with the one or more anchoring members that are resiliently deflectable in a direction in-plane with the wafer in which the anchors are formed. In another aspect, the anchoring members may include one or more expandable mechanical features such as memory shaped alloy (e.g. Nitinol loop) that is clamped into a silicon wafer of the sensor device or may include a polymer expandable mechanical layer in the device.

In still other embodiments, the sensor device may include at least a first and second anchoring member such that anchoring includes deploying the first anchoring member along the sclera outside of the vitreous body and deploying the second anchoring member along the sclera inside the vitreous body so as to inhibit axial movement of the IOP sensor along the insertion axis in both proximal and distal directions after implantation. Each of the first and second anchoring members may include one or more anchoring members. In another aspect, anchoring against rotation of the sensor device may be provided by the shape of the sensor device itself. For example, in some embodiments, the sensor device may be formed with a cross-sectional shape that is not axi-symmetric along a longitudinal axis of the sensor device, for example, a square or rectangular cross-section, so as to inhibit rotation of the device along its longitudinal axis. This feature allows for improved charging and telemetry by allowing the user to stabilize the position at which the charging and telemetry components of the sensor device are positioned.

In another aspect, methods for extracting the implanted sensor device are provided. Such methods may include extracting the IOP sensor by attaching an instrument to an extraction feature coupled to a proximal end of the IOP sensor disposed outside the vitreous body. In an embodiment where the sensor device has first and second anchors, extraction may include pulling the extraction feature until an anchoring force provided by the at least second anchoring member is overcome.

Methods of anchoring an implant are also provided. Such methods may include inserting an implantable device through a distal tip of an injector or syringe along an insertion axis into a body tissue or body space within a patient, the device being formed, at least in part, by a wafer process and deploying one or more anchoring members of the device so as to extend laterally outward from the insertion axis to inhibit movement of the implanted device within the body tissue or body space. The one more anchoring members may include a portion of a wafer of the device defined so as to be resiliently deflectable in a direction in-plane with the wafer. Inserting the implantable device may include constraining the one or more anchoring members within the distal tip or a sheath in a position deflected toward the insertion axis, the insertion axis being in-plane with the wafer defining the one or more anchoring members. Deploying the one or more anchoring members may include releasing the one or more anchoring members from the constraining distal tube or sheath when the device is positioned in a desired position within the body tissue space. The sensor may be positioned within a target region in the patient in which a physiological measurement is desired by injecting the sensor into the target region so that the entire sensor portion is disposed within the region. In some embodiments, the method may include penetrating a distal tip of an injector or syringe through a tissue wall of the patient along an insertion axis, wherein the sensor is injected through the distal tip of the injector or syringe. Such injectable sensors may include any of the features described herein and may be implanted, anchored or extracted according to any of the methods set forth herein.

The details of one or more implementations are set forth in the accompanying drawings and the description below. Other features will be apparent from the description and drawings, and from the claims.

BRIEF DESCRIPTION OF THE DRAWINGS

FIGS. 6A-6B through 9A-9B illustrate example implantable sensor devices and views of the example devices after implantation in accordance with embodiments of the invention.

FIGS. 15A-17C illustrate example implantable sensor devices in accordance with embodiments of the invention.

DETAILED DESCRIPTION OF THE INVENTION

Figure 1:
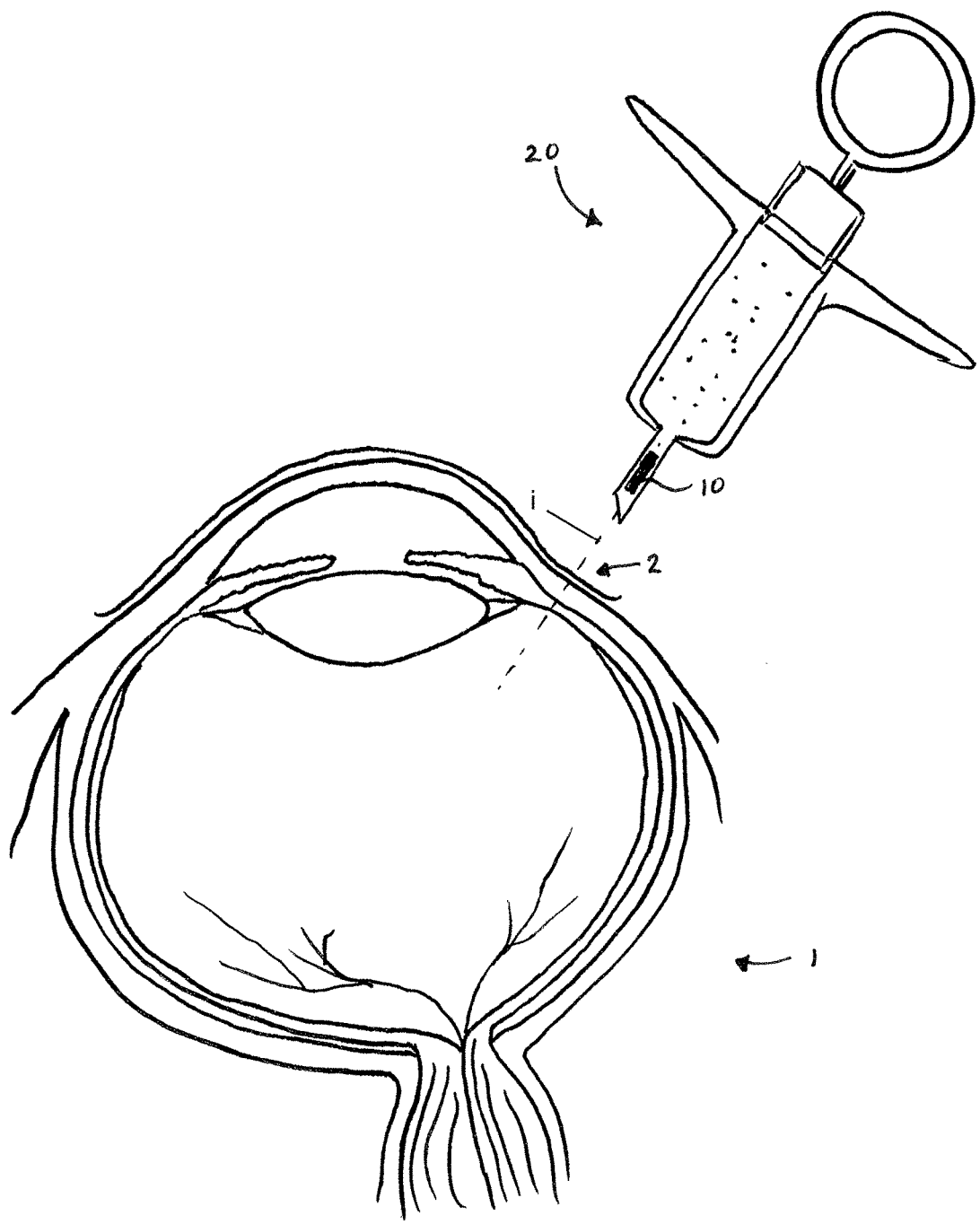
FIG. 1 is an illustration of a method of implantation in accordance with embodiments of the invention.

FIG. 1 is an overview illustration of a sensor implantation method in accordance with embodiments of the present invention. In particular, the depicted method relates to implantation of an IOP sensor device 10 within an eye 1 of a patient by injecting the IOP sensor device 10 into the eye with a fluid-filled syringe 20 or injector. In one aspect, the IOP sensor device is positioned within the vitreous body of the eye 1 by penetrating the conjunctiva and sclera with a distal tip of a needle of a syringe 20 along insertion axis I extending through the ora serrata region 2. Implanting the sensor device by injection at this location is advantageous over conventional implantation methods as it avoids the potential for damaging the delicate structures within the anterior chambers and as well as damage to the photosensitive tissues of the retina.

In one aspect, the injectable sensor can be implanted in a physician's office without surgery, such as by a relatively simple injection procedure using a standard needle size (e.g. 19 gauge). Once implanted the sensor device can provide continuous monitoring, up to one week or several weeks between charges. The system may include an external patient data acquisition unit that is used to charge the implanted sensor, collect and store data from the implanted sensor, and transmit the collected IOP data to a data server for further analysis and monitoring (e.g. the cloud or other server). The data may be available to the patient and/or the patient's treating physician at any time. The external patient data acquisition unit may be incorporated into a personal mobile device, such as a smart-phone. These aspects are further described in U.S. Non-Provisional patent application Ser. No. 14/789,942, entitled "Ultra Low Power Charging Implant Sensors with Wireless Interface for Patient Monitoring."

Figure 2A:
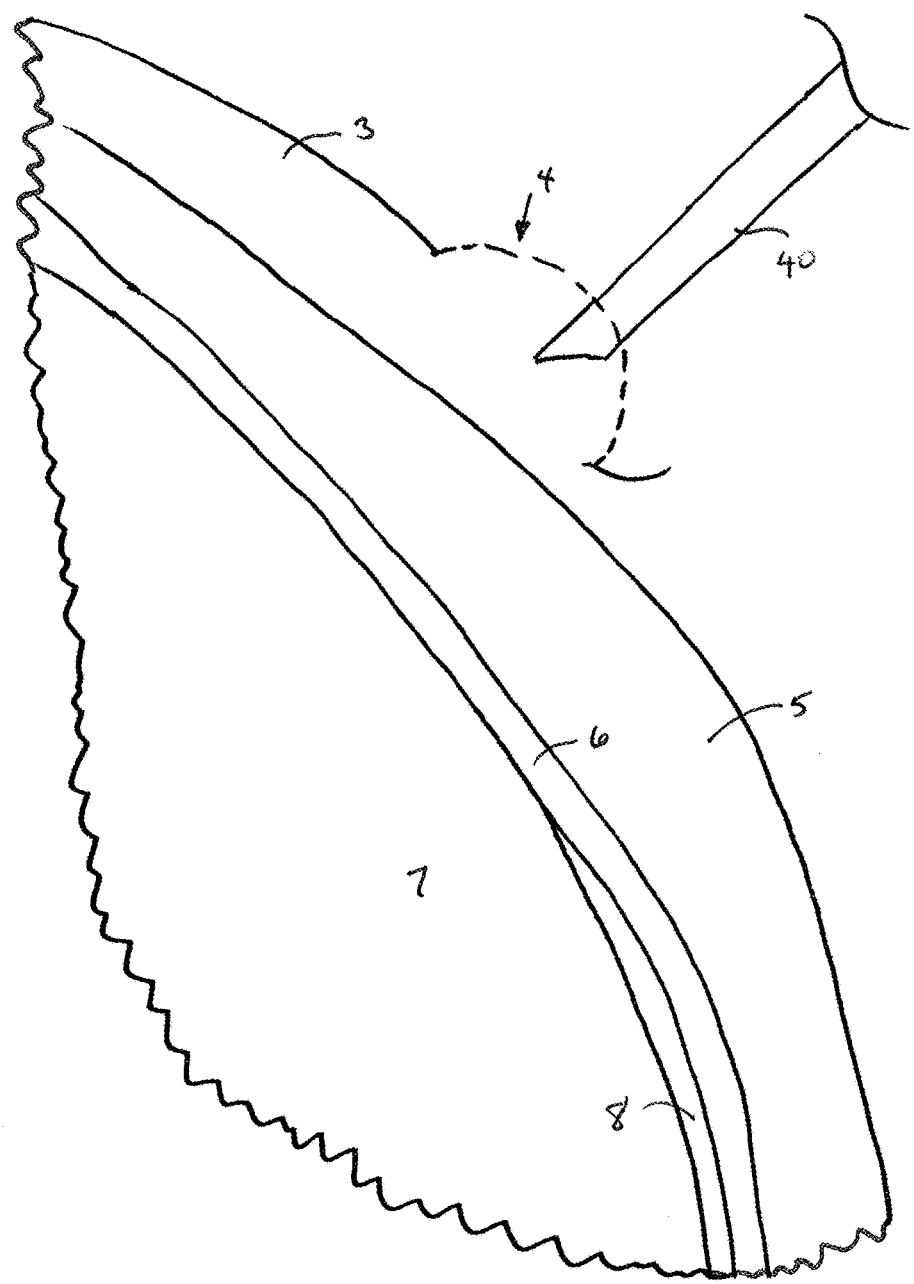
FIGS. 2A-2D illustrate sequential steps of an implantation method in accordance with embodiments of the invention.

FIGS. 2A-2D illustrate sequential steps of a method of implanting an IOP sensor within a vitreous body of an eye 1 in accordance with the approach described above in FIG. 1. As shown in FIG. 2A, a fluid is injected into the conjunctiva 3 in the ora serrata region of the eyeball through injection needle 40 to form a ballooned portion 4 of the conjunctiva. The fluid may be saline and/or may include a numbing or anesthetic to reduce sensitivity in the eye 1 prior to penetrating the layers of the eye during implantation. The conjunctiva is the mucous membrane that lines the inner surface of the eyelids and is continued over the forepart of the eyeball. The ballooned portion facilitates deployment of the sensor device against the sclera and allows the conjunctiva to cover the proximal anchoring portion of the sensor device after implantation, as will be described in further detail below.

Figure 2B:
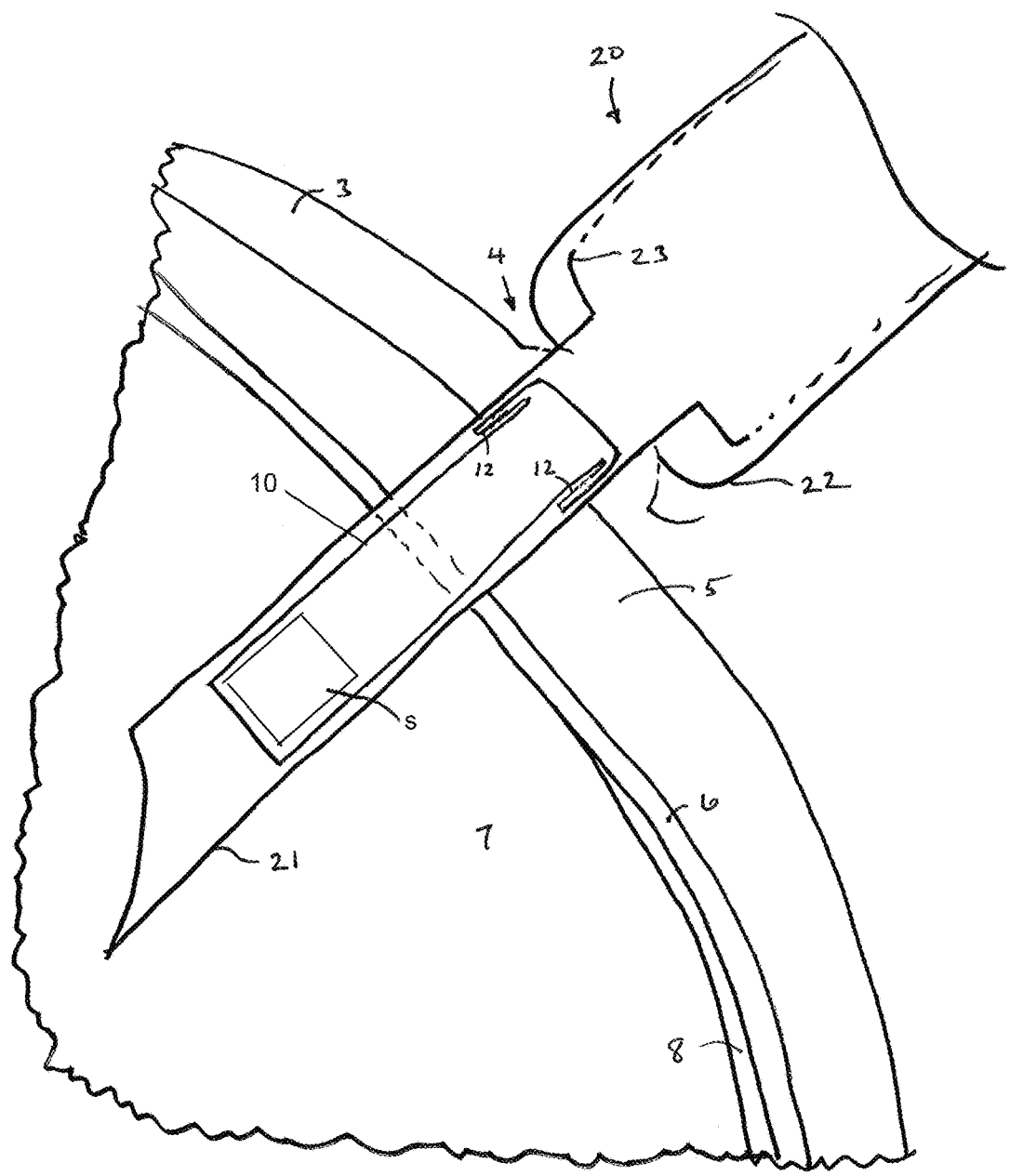

As shown in FIG. 2B, a distal tip 21 of the fluid-filled syringe or injector 20 is penetrated through the ballooned portion 4 of the conjunctiva and through the sclera 5 and the choroid 6 until the distal tip 21 is positioned within the vitreous body 7. The sclera 5 is the dense fibrous opaque white outer coat enclosing the eyeball except the part covered by the cornea (not shown), while the choroid 6 is the vascular layer extending between the retina 8 and the sclera 5 to the ciliary body and iris (not shown) of the eye 1. The IOP sensor 10 is disposed within the distal tip 21 of the fluid-filled syringe and may include one or more anchoring members 12 constrained within the distal tip to be deployed upon release (e.g., self-expanding). The distal tip 21 is advanced distally along the insertion axis until a distal facing surface of the syringe 22 abuts against the ballooned portion 4. The distal tip 21 is then refracted into the syringe 20 such that displacement of fluid within the syringe causes the sensor device 10 to maintain its position while the distal tip 21 is refracted, thereby releasing the sensor device from the syringe or injector 20.

Figure 2C:
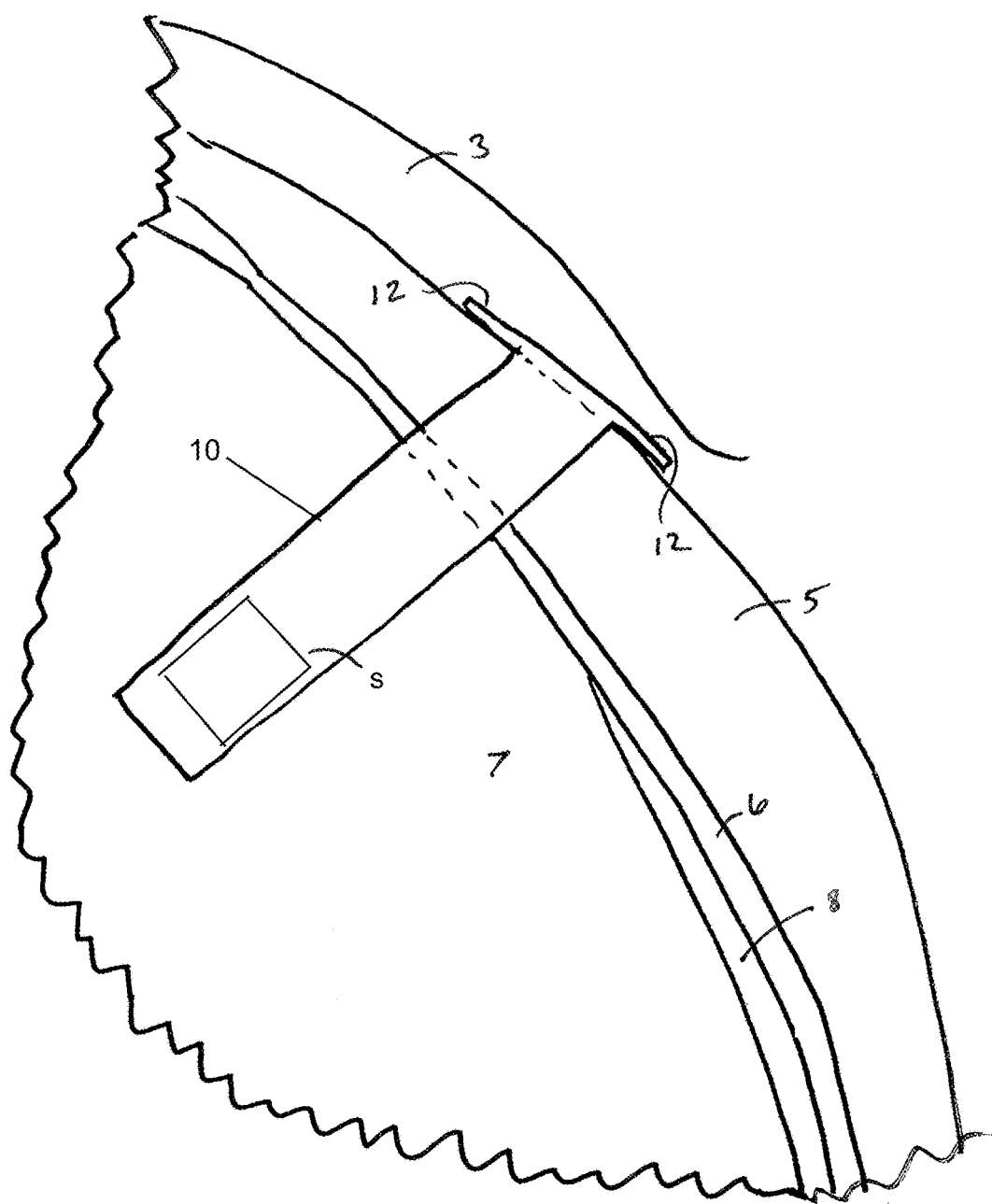

A shown in FIG. 2C, after release from the distal tip 21 of the syringe 20, the anchoring members 12 resiliently extend laterally outward from the insertion axis against the outer surface of the sclera 5. This anchoring configuration substantially maintains the position of the sensor diaphragm s of the device 10 at the desired location so that an IOP sensor near a distal end of the sensor device remains entirely within the vitreous body, such as shown in FIGS. 2B and 2C. By extending the anchoring members along the sclera outside the vitreous body, the anchoring members 12 prevent the sensor device 10 from potentially slipping into the vitreous body, which could cause damage to the retina or optic nerve 9.

Figure 2D:
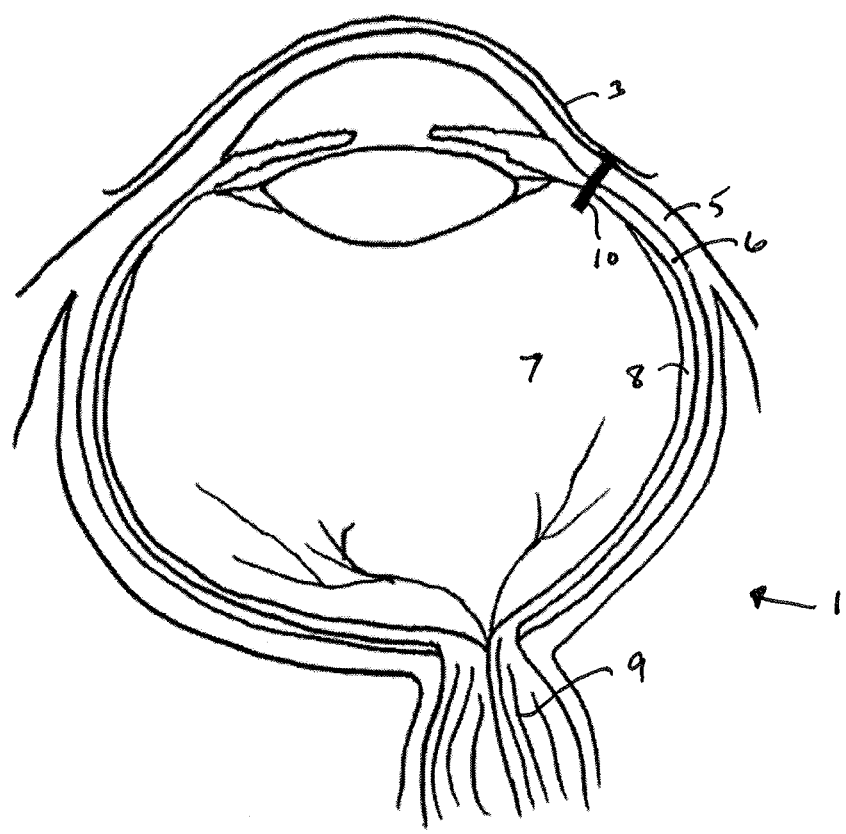

FIG. 2D shows the sensor device 10 implanted within the eye. In certain aspects, the sensor device 10 is configured such that a particular alignment (e.g. rotational) is not required to facilitate charging and/or wireless communication with the device. For example, so long as the sensor device 10 is implanted into the eye so that the sensor s is disposed within the targeted region and the sensor device 10 is anchored near the sclera, the charging and communication coils are in close enough proximity such that an external device positioned near the eye can establish sufficient magnetic coupling so as to charge and/or communicate with the device. Nonetheless, in another aspect, for certain configurations, it may be useful to provide methods that control alignments/orientation for the sensor device when implanted for various reasons, such as to optimize charging or improve communication. In such cases, the orientation of the can be controlled by providing the sensor device in a substantially fixed or at least a known orientation within the distal tip such that controlling the orientation of the syringe or injector during implantation controls orientation of the sensor 10. For example, if the sensor orientation is known, the syringe can be marked (e.g. a line or arrow) so that the physician can visually align the syringe in a desired location to control orientation of the implanted sensor device 10.

Figure 3A:
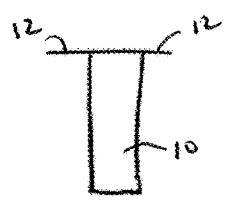
FIGS. 3A-3C illustrate an implantable sensor device before, during and after implantation in accordance with embodiments of the invention.
Figure 3B:
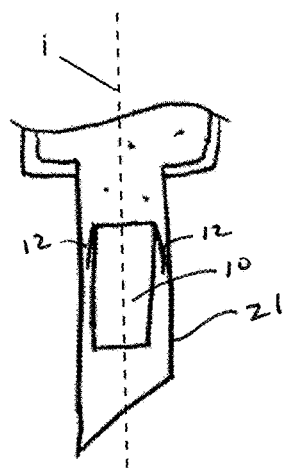
Figure 3C:
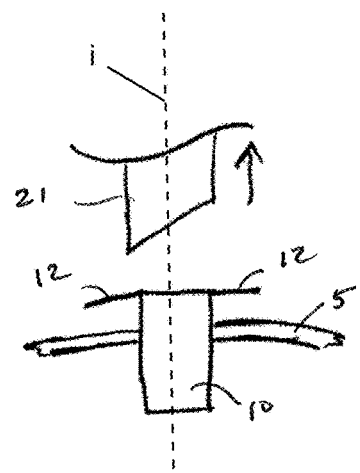

FIGS. 3A-3C illustrate an example sensor device 10 having two anchoring members at a proximal end thereof, which have a bias in a lateral direction. As shown in FIG. 3A, the anchoring members 12 extend laterally outward from an insertion axis i along which the sensor 10 is implanted. Although the anchoring members are shown as extending substantially perpendicular to the insertion axis, it is appreciated that the anchoring members could configured to extend along other angles (e.g. 30, 45 or 60 degrees from the insertion axis) according to a desired anchoring configuration or as needed for a particular application. In one aspect, the sensor device is formed, at least in part, using wafer processing methods, such that the anchoring members may be defined as features of a wafer or substrate of the sensor device. For example, the sensor device may be formed on a silicon substrate and the anchoring members may be defined as features of the silicon substrate using wafer processing methods, such as deep etching. In addition, various wafer fabrication methods may be used to round or soften any sharp corners of the sensor device to avoid damage to eye tissues after implantation.

In one aspect, the sensor device is formed, at least in part, on a rigid substrate, such as a silicon wafer. Although the substrate may be substantially rigid, portions of the substrate, such as those portions defining the one or more anchoring members, may be processed so as to alter a mechanical property as desired. For example, a wafer processing method may be used to define the anchoring members with a desired thickness and/or width so that the anchoring members become semi-rigid or flexible. This allows the one or more anchoring members to be sufficiently flexible in a direction in-plane with the device so as to bend alongside the sensor device when constrained within a distal tip of a needle, such as shown in FIG. 3B. Preferably the sensor device is sufficiently small enough to be injected through a needle (e.g. gage of 19 or higher) along a direction in-plane with sensor device. Once the distal tip 21 of the syringe is retracted, the anchoring members 12 resiliently return to their laterally extended configuration, as shown in FIG. 3C, so that when pushed distally along the insertion axis, the anchoring members engage an outer surface of the sclera, thereby preventing further distal movement of the sensor device. In one aspect, the conjunctiva covers and heals over the proximal surface of the sensor device such that the conjunctiva inhibits movement of the implanted sensor device in the proximal direction while the anchoring members inhibit movement of the implanted sensor in the distal direction.

Figure 4A:
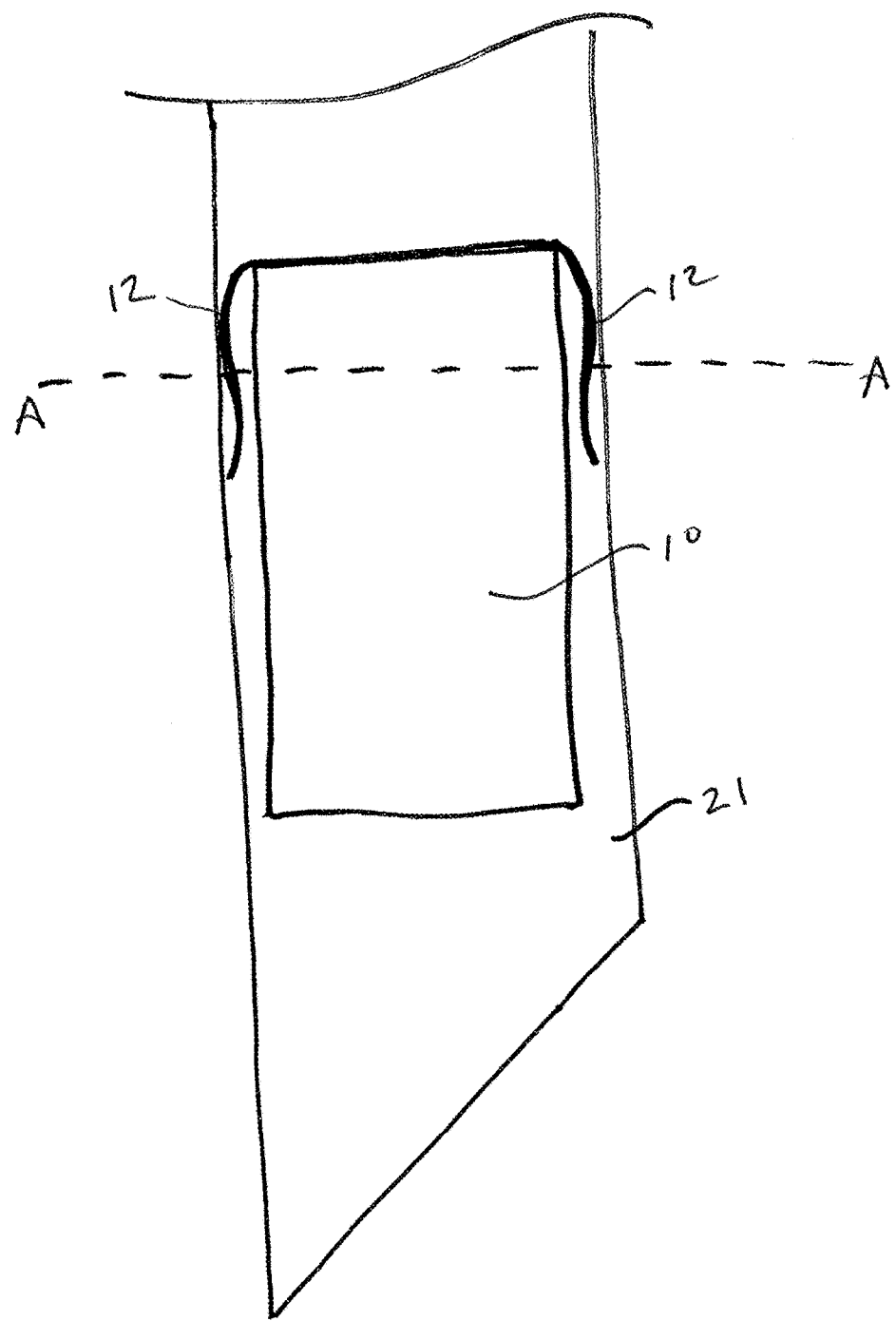
FIG. 4A and FIG. 4B illustrate an implantable sensor device constrained within an implantation device and an associated cross-sectional view in accordance with embodiments of the invention.
Figure 4B:
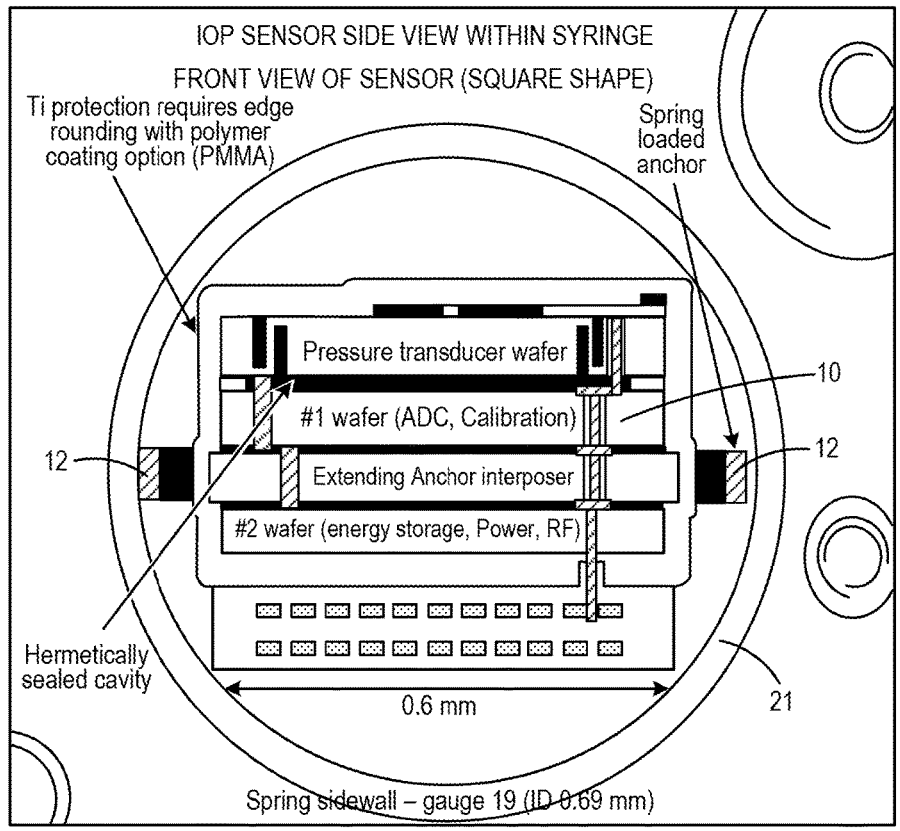

FIG. 4A illustrates a detail view of a sensor device 10 having two resiliently deflectable anchoring members 12 at a proximal end of the device 10, which are constrained within the distal tip 21 of the syringe or injector. FIG. 4B illustrates a cross-sectional view of the sensor device of FIG. 4A constrained within the distal tip 21 of the syringe. As can be seen, the sensor device 10 comprises a vertically-stacked device formed, at least in part using wafer fabrication methods. The anchoring members 12 may be formed from a portion of a rigid substrate, such as a silicon wafer. Typically, the anchor is defined its own substrate material separate from the MEMS pressure sensor wafer. In one aspect, a MEMs device is supported on a rigid substrate that defines at least a part of the sensor. Forming the sensor on a rigid substrate may improve the integrity, accuracy and longevity of the MEMs device, while defining various other portions of the rigid substrate to be flexible allows for improved anchoring and/or deployment as needed for a given application. While a certain configuration of sensor, in particular a sensor having a vertically stacked architecture, it is appreciated that various other configurations may be utilized in accordance with the implantation methods described herein. For example, the device may include a vertically stacked architecture such as those shown in FIG. 5 of U.S. Non-Provisional patent application Ser. No. 14/789,839, entitled "Hermetically Sealed Implant Sensors with Vertical Stacking Architecture," filed concurrently herewith.

In certain aspects, the anchoring members are defined in a portion of the wafer that is thinned down (e.g. thinned to a 100 µm range) and that passes all electrical connections using TSV (through silicon vias). The electrical connections are sealed from the body fluid/media using a seal ring similar to the one used between MEMS wafer and CMOS wafer. The portion extending through the die area that will define the anchoring members will extend and typically etched using a process called DRIE to create the desired shape. This process may be done when all the wafers are bonded together so as to process them in a batch mode. The anchoring members are formed such that they are extended when the wafers are stacked, which creates a fairly wide spacing between each die. In one aspect, before dicing, all edges are rounded with a wet etch (isotropic) to create soft corners and avoid sharp edges that may need to be eliminated to reducing tissue damage. To facilitate the dicing, the anchors are typically pre-etched (DRIE) and formed before the interposer is bonded. After the stack (CSP) is created via bonding, the dicing will cingulated each die but they will be left on blue-tape for pick and place. Each die with extended anchoring members is pushed into the syringe such that the anchoring members fold against the sidewall of the syringe. The angle and length of the anchoring members determines how much anchoring force the anchoring members provide against the tissue. In some embodiments, the anchoring members are formed to provide an anchoring force within a range of 100 to 1,000 µN. It is appreciated that while such configurations are particularly useful for anchoring of the described sensor device 10 within the eye, various other configurations of anchoring members may be utilized, including anchoring members with sharpened edges (e.g. barbs), so as to facilitate anchoring within various other tissues. Such configuration may be particularly useful in sensor devices implanted in various other locations within the human body.

Figure 5A:
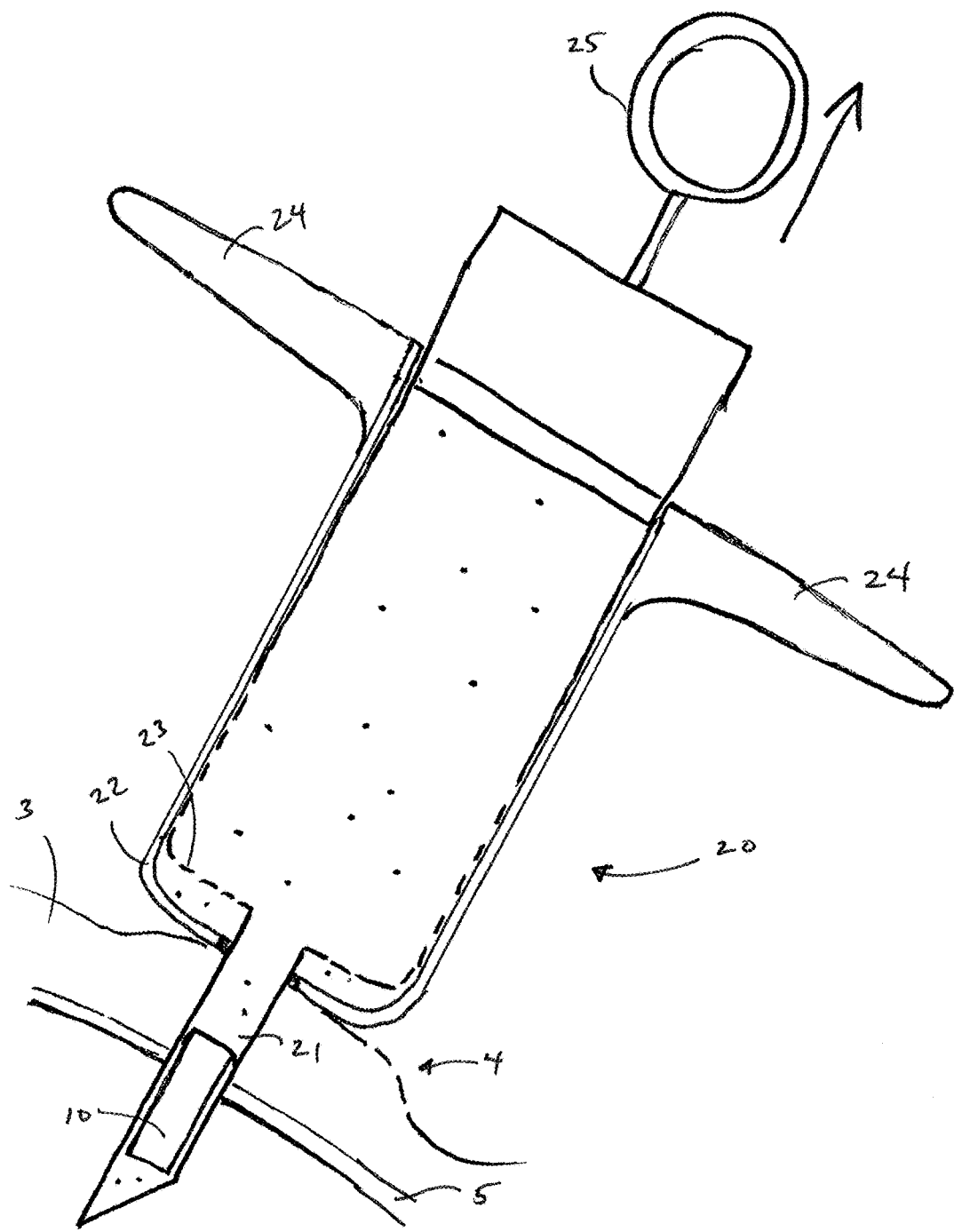
FIGS. 5A-5B and FIGS. 5C-5D illustrate an injector syringe used in two implantation methods, respectively, in accordance with embodiments of the invention.
Figure 5B:
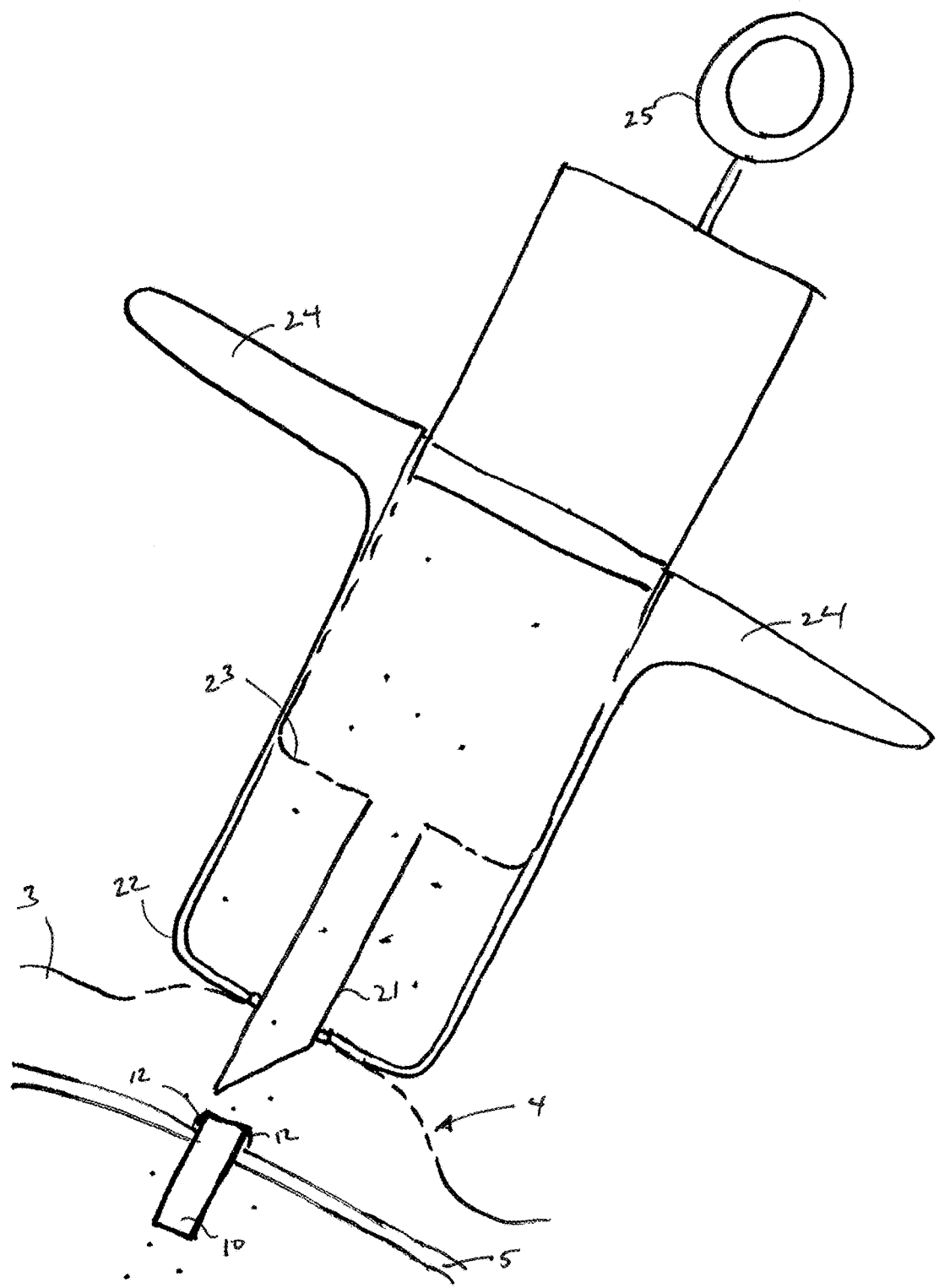
Figure 5C:
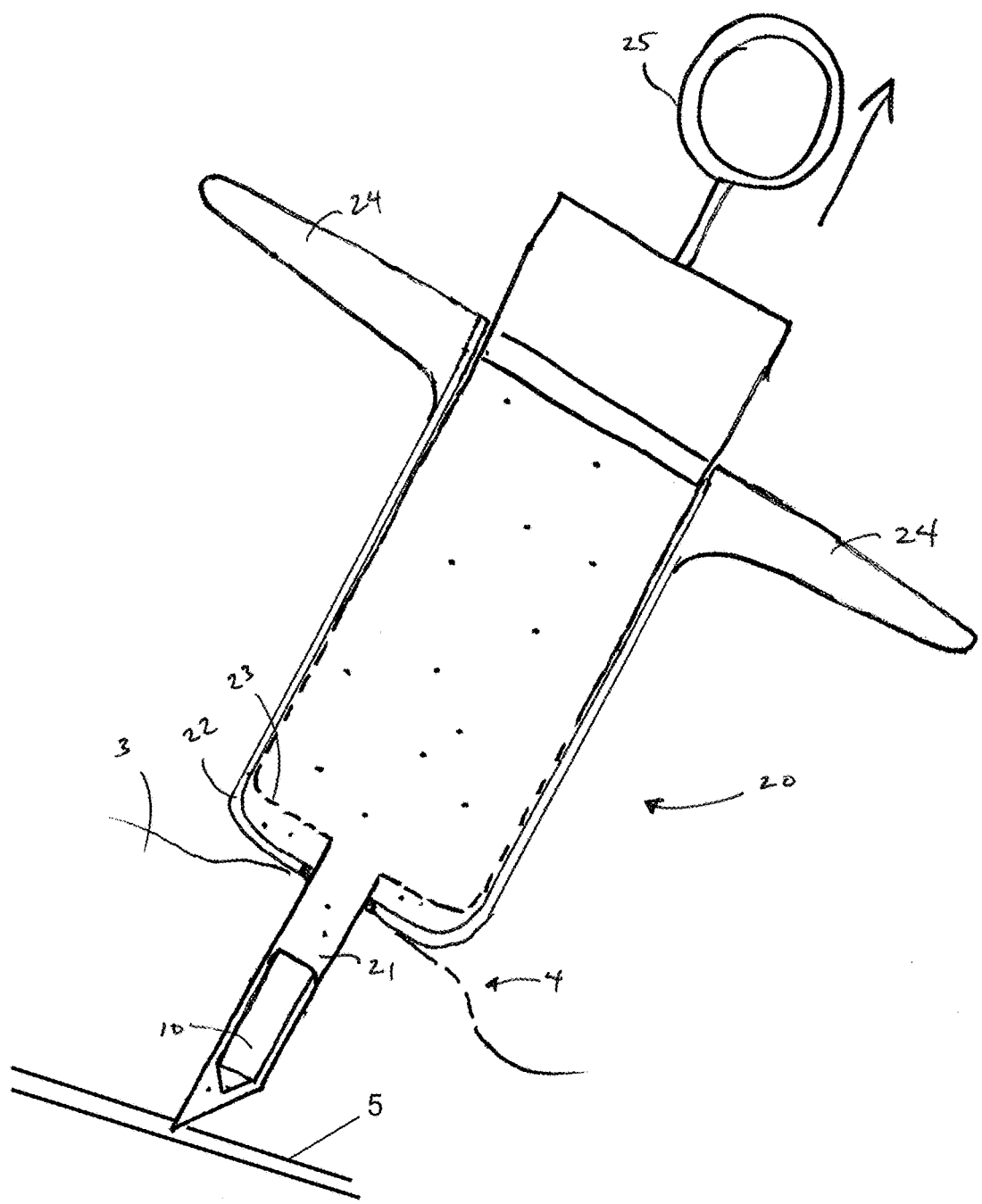
Figure 5D:
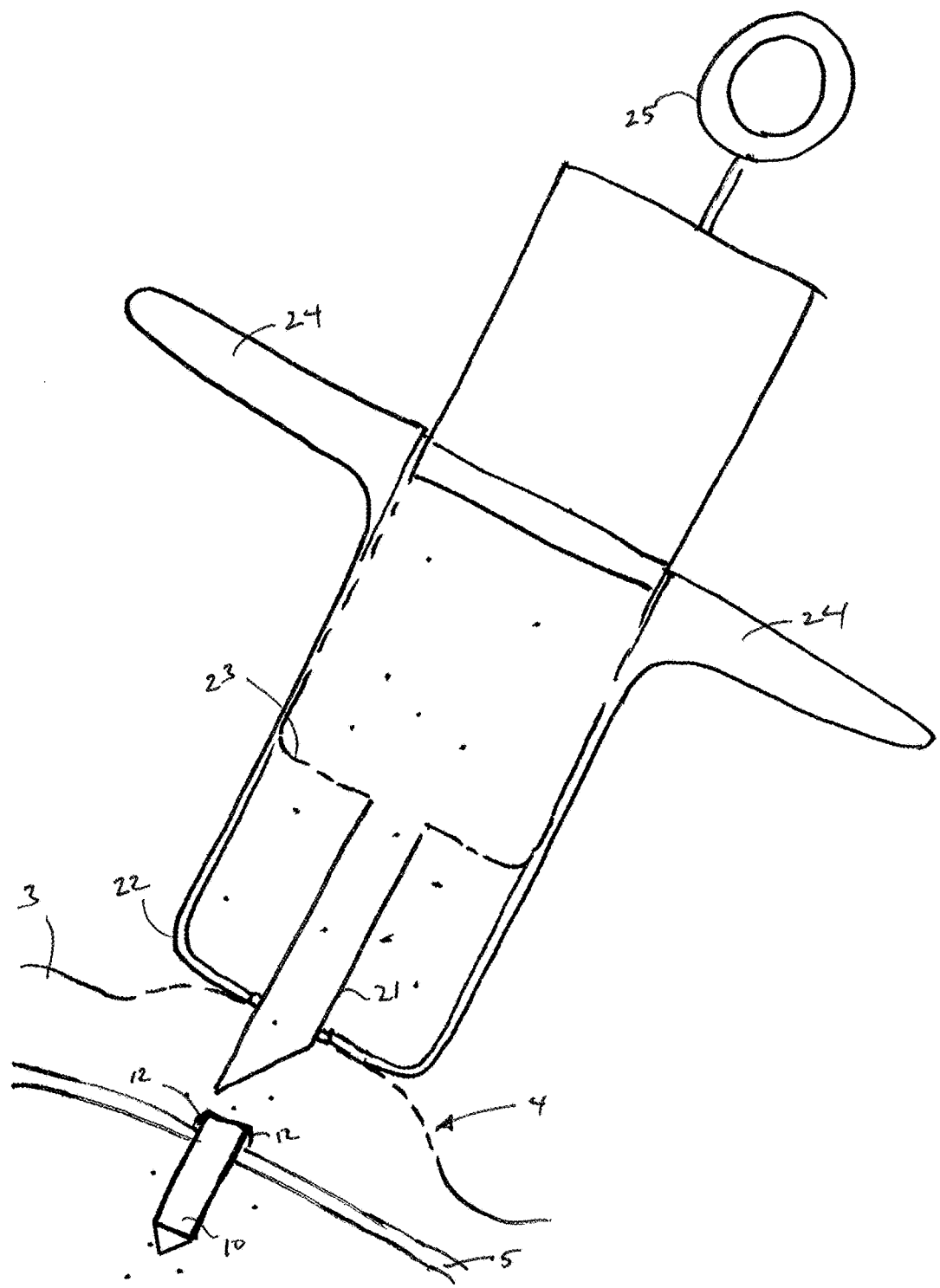

FIGS. 5A-5B depict a syringe 20 or injector used in accordance with the sensor implantation methods described above. The syringe 20 may include an outer cylinder having a distal facing surface 22 and an inner cylinder 23 slidably disposed within. The syringe 20 may be provided to a surgeon pre-sterilized and pre-filled with a fluid and a sensor device fixed within the distal tip 21 of the syringe. The sensor device 10 may be releasably positioned within the distal tip 21 and may be held in place by force of the resilient anchoring members constrained within. After penetration of the sclera with the distal tip, the distal tip 21 as well as the inner cylinder attached thereto can be retracted, such as by pulling a proximal feature 25 (e.g. thumb ring) attached to the inner cylinder in a proximal direction while maintaining the outer cylinder position with the fingers against stabilizer 24. As the volume of the syringe is reduced, the fluid within the syringe is displaced, which moves the sensor device relative the distal tip during retraction so that the sensor device 10 substantially maintains its position and is released from the distal tip 21 as shown in FIG. 5B. Upon release of the sensor device 10 from the distal tip 21, the anchoring members 12 deploy laterally outward thereby anchoring the sensor device against the sclera. In some embodiments, the sensor device 10 may be pushed distally after deployment to facilitate engagement of the anchoring members 12 against the sclera and coverage of the anchoring members with the ballooned portion of the conjunctiva. FIGS. 5C-5D depict a syringe 20 or injector used in accordance with another implantation method, which is similar to that described above in FIGS. 5A-5B expect the needle or distal tip of the injector does not penetrate through the sclera. Rather, the distal tip is partly inserted into the sclera and the sensor device is advanced, in a similar manner as described above, such that a distal tip of the sensor device continues to advance through the sclera and into the vitreous body.

FIGS. 6A-9A illustrate alternative example sensor devices having differing anchoring configuration and FIGS. 6B-9B illustrate each of the examples after implantation. In some embodiments, the sensor device 10 may include anchoring members disposed on opposite sides of the sclera, such as shown in FIGS. 7A1, 7A2, 8A1, 8A2 and 9A, which may provide additional anchoring in both proximal and distal directions, as can be understood by referring to their deployed positions as shown in corresponding FIGS. 7B1, 7B2, 8B1, 8B2, and 9B, respectively.

Figure 10A:
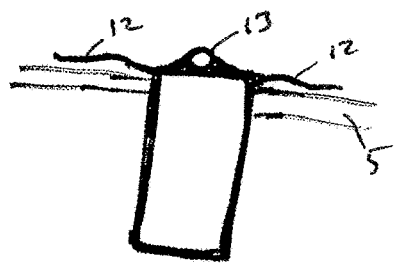
FIGS. 10A-10C illustrate sequential steps of an explantation of an implanted sensor device using an explantation tool in accordance with embodiments of the invention.
Figure 10B:
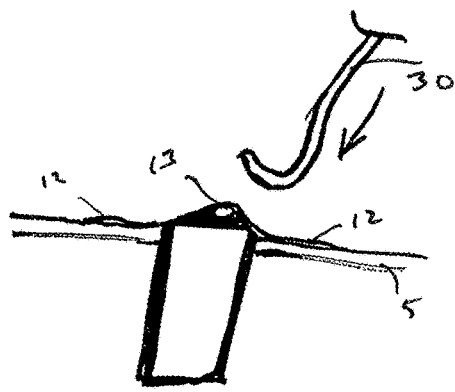
Figure 10C:
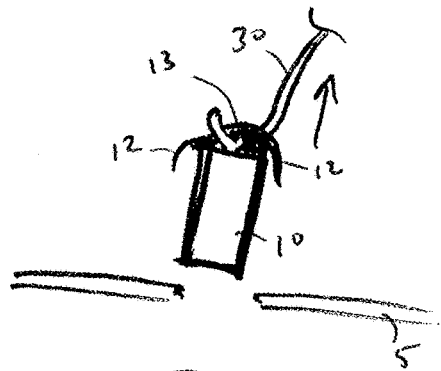

In another aspect, the sensor device 10 may include an extraction feature 13 that facilitates extraction of the sensor after implantation. The extraction feature 13 may include a hole or loop feature that interfaces with an extraction tool 30 to allow the sensor device 10 to be pulled in a proximal direction and extracted from the eye. The extraction feature 13 may include a separate feature attached to the device 10 or may be integrally formed with the device itself. In embodiments where the anchoring members are defined portions of a substrate or wafer of the sensor device, the extraction 13 may be defined in a different portion of the same substrate or wafer. For example, as shown in FIG. 10A, the anchoring members 12 are S-shaped portions of a rigid substrate, such as a silicon wafer, and the extraction feature 13 is a hole or opening formed within the same layer. The hole is dimensioned to allow an extraction tool 30, such as a hook-like tool, to be inserted within the hole to allow the implanted sensor device 10 to be proximally pulled and extracted from the eye.

Figure 11:
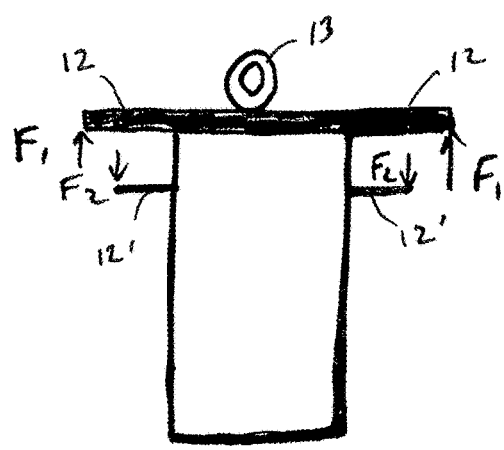
FIGS. 11-13 illustrate examples of an implantable sensor device in accordance with embodiments of the invention.
Figure 12:
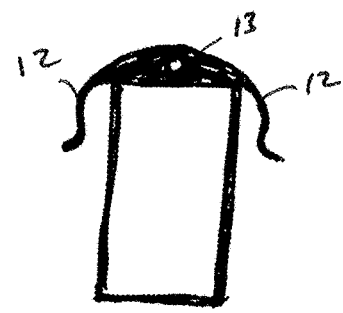
Figure 13:
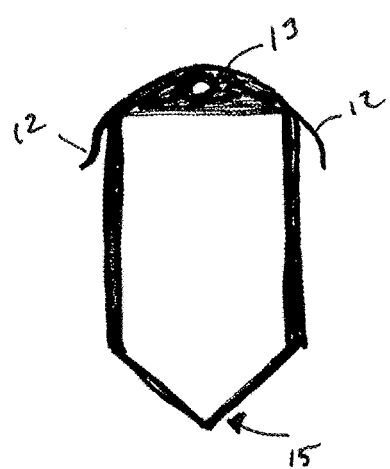

FIGS. 11-13 illustrate additional examples of sensor devices 10 in accordance with implantation methods of the invention. FIG. 11 illustrates a sensor device 10 having two anchoring members 12 for engaging an outer surface of the sclera and two additional anchors 12' for engaging an inner surface of the sclera, as well as a proximal extraction feature. In one aspect, the anchoring members 12, 12' are dimensioned so that the anchoring members 12 that engage an outer surface of the sclera provide an anchoring force F1 that is greater than an anchoring force F2 provided by the anchoring members 12' that engage an inner surface of the sclera. This configuration allows for improved anchoring in both distal and proximal directions along the insertion axis, while still allowing for extraction by proximally pulling the extraction feature 13 until force F2 is overcome. FIG. 12 illustrates a sensor device 10 having an S-shaped anchoring member 12, which may be defined so as to provide a spring-like resistance when pushed against the sclera.

Figure 14A:
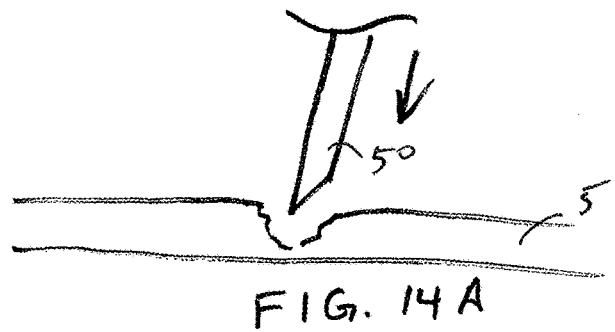
FIGS. 14A-14C illustrate sequential steps of an example implantation method in accordance with embodiments of the invention.

FIG. 13 illustrates a sensor device 10 having anchoring members 12 and an extraction feature 13 at a proximal end of the device 10 and a penetrating tip 15 formed at the distal tip. In some embodiments, the penetrating tip 15, anchoring members 12 and extraction feature 13 are each formed within a different portion of the same layer, such as a rigid substrate (e.g. a silicon wafer) of the device. Each of the features may be formed using wafer processing techniques such as deep plasma etching. An example of how such a penetrating tip 15 can be used is shown in the implantation method shown in FIGS. 14A-14C.

Figure 14B:
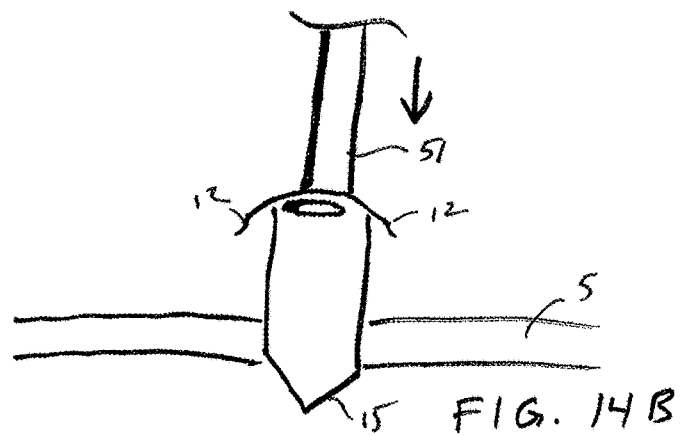
Figure 14C:
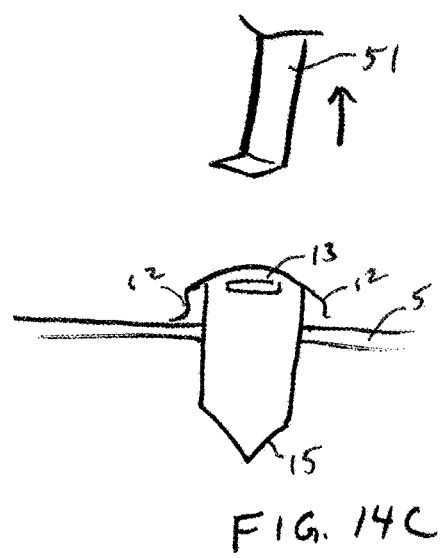

In some embodiments, the sensor device 10 can be implanted by injecting with a tool or device other than a fluid-filled syringe. In the example method shown in FIG. 14A, the sclera is partly penetrated by a tool 50 leaving only a thin or weakened portion of the sclera. The sensor device is then advanced distally in this region until the penetrating tip 15 of the sensor device 10 penetrated through the sclera and into the vitreous body, as shown in FIG. 14B. The sensor device is advanced until the anchoring members 12 engage the sclera, as shown in FIG. 14C. The sensor device 10 may be advanced using a pusher tool 51 that interfaces with the extraction feature 13 such that the extraction feature facilitates implantation and extraction. In this embodiment, the extraction/implantation feature 13 may be oblong in shape, such as a slot, so as to improve stability and prevent rotation or twisting of the sensor device when being pushed through the sclera with the pusher tool 51. In one aspect, this approach allows for a variety of alternative anchoring configurations since it does not require that the anchoring members be constrained within a distal tip of a syringe. For example, the anchoring members 12 could be relatively fixed in a laterally outward configuration, which may allow for thicker or more rigid anchoring members to be used if desired.

FIGS. 15A-15D illustrate views of an alternative example sensor device 10 having a distal penetrating tip 15 for advancing through the sclera such as in the implantation method described above and an explantation feature 13 at the opposite end. This embodiment does not include the anchoring members described above. Such an embodiment may be useful in an application where anchoring is not desired or needed, for example, when used with a shunt that is self-anchoring within the eye.

Figure 16A:
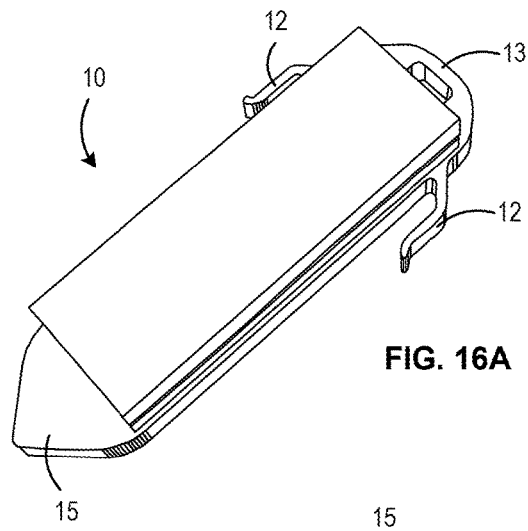
Figure 16B:
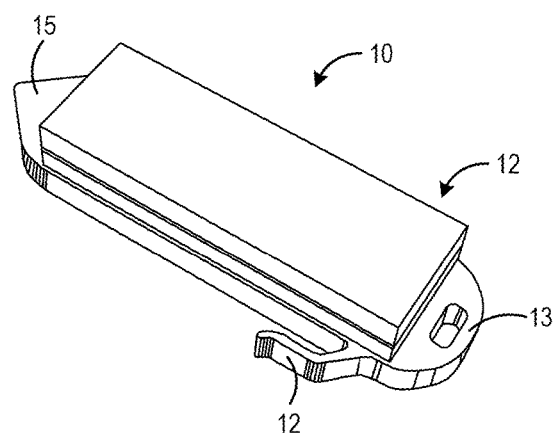
Figure 16C:
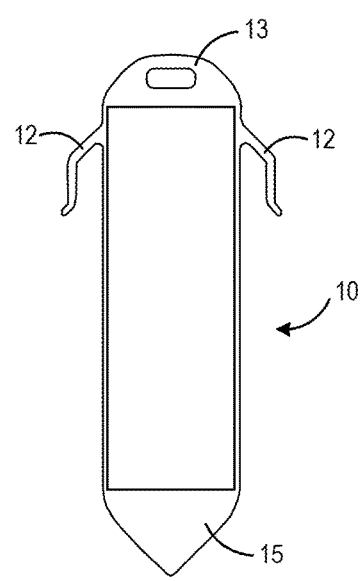

FIGS. 16A-16C illustrate views of an example sensor device 10 formed with a vertically stacked architecture. A wafer or substrate extending through the device is defined to have a penetrating tip 15 for advancing through the sclera defined at the distal end of a wafer and an explanation feature 13 and anchoring members 12 defined in the same wafer at a proximal end of the device 10. In one aspect, the vertically stacked architecture of this device may be the same as that shown in FIG. 5 of U.S. Non-Provisional patent application Ser. No. 14/789,839, entitled "Hermetically Sealed Implant Sensors with Vertical Stacking Architecture."

FIGS. 17A-17C illustrate various view of an alternative design of a sensor device 100 in accordance with embodiments of the invention. In this alternative design, the distal penetrating tip of the sensor device and the anchoring features are integral parts of a support structure or boat in which the wafer-stacked sensor device resides and is bonded thereto. While the distal penetrating tip and/or the anchoring features are described herein as being parts of an interposer layer or a boat support structure, it is appreciated that these components may be configured in various other ways, including separately formed structures that are bonded to the sensor device after fabrication.

The implantable device 100 comprises vertically stacked heterogeneous components, namely a first MEMS wafer or die 112 and a second CMOS wafer or die 114. The first wafer 112 comprises at least a pressure sensor configured to measure IOP on a frequent or desired basis (e.g., 1 sample per hour, 2-4 samples per day, etc.). The second wafer 114 comprises at least a digitizing ASIC. In some embodiments, the ASIC includes a microcontroller to enable firmware update of the implant, customization of sampling function (rate/window, accuracy, resolution, etc), auto-adaptive sampling to measured pressure, built-in self-test, error detection and correction, embedded diagnostics, broad use models with on-demand sample, streaming data and autonomous mode. The first MEMS wafer 112 is vertically stacked or disposed over the second CMOS wafer 114 so as to form a first hermetic seal. In particular, the vertical stacking of the wafers is configured to create a hermetically sealed cavity between the MEMS 112 and CMOS wafers 114 of the implantable device 100. In some embodiments, the stack includes one or more additional wafers, for example one or more wafers adapted for use as a power source. Such embodiments may include a third wafer that includes a supercapacitor. In some embodiments, the stack further includes a fourth wafer that includes a battery. Such embodiments may utilize a power management scheme switching between the supercapacitor and battery in order to prove more efficient power discharge from a high impedance thin-film battery, such as a LiPON battery. An example of such a configuration is shown in the embodiment in FIGS. 17A. As can be seen in the cross-sections A-A and B-B in FIGS. 17B and 17C, respectively, the stacked sensor device of FIG. 7A includes the MEMS 112 and CMOS wafers 114, a decoupling capacitor wafer 113 and a thin film battery/energy storage wafer 115. In one aspect, the wafers of the stack may be bonded together with low temperature Gold-Indium (Au—In) bond, while the cavities are formed using a silicon-to-silicon fusion bond. This configuration provides improved thermal budget management, while the silicon-to-silicon fusion bond provides long term vacuum stability (e.g. greater than 20 years). In this embodiment, rather than an interposer layer, the stacked device is placed within a support structure or boat 119. The boat can include integral anchor features 121 for engaging proximal and distal sides of the sclera while the IOP sensor portion is maintained within the vitreous body.

In this embodiment, the IOP sensor device 100 includes a reference sensor 123 disposed adjacent the IOP sensor 122, as shown in FIG. 17C, the reference sensor 123 being configured for detecting one or more second order effects so as to allow cancellation of the second order effects from the pressure measurement obtained from the IOP sensor 122. In one aspect, the IOP sensor and the reference sensor are of a substantially similar construction having a cavity, except the cavity of the IOP sensor is under vacuum such that the sensing diaphragm is sensitive to changes of pressure such that a signal from the IOP sensor corresponds to changes in pressure and the corresponding cavity of the reference sensor is filled such that a signal obtained from the reference sensor corresponds to the second order effects. In some embodiments, methods of obtaining IP measurements with such a device include cancelling the second order effects associated with the IOP measurement obtained from the IOP sensor using the signal from the reference sensor. Such methods can further include embedding data within the IOP measurement relating to the second order effects detected by the reference sensor, wherein the second order effects are associated with at least one of temperature and stress in the sensor device.

In some embodiments, the anchoring structure is formed in a separate support structure or "boat" in which the diced multi-wafer stack is placed and attached with low temperature metal alloy. An example of such a "boat" can be seen in the embodiment of FIG. 17A. In some embodiments, this support structure or boat may also include a distally tapered tip 120 to facilitate penetration through the sclera during implantation and may also include one or more anchoring features 121. Such features may be included as components with a mechanical function that clamps onto the sclera (e.g. a proximal and distal anchor on opposite sides of the sclera). The anchoring feature may also include an anchoring loop or extensions. Such anchoring features may be formed of Silicon, Titanium, shape memory alloy, or other suitable materials. In some embodiments, the boat is formed of a monolithic material and include side-walls that extend upwards, at least partly, along a thickness dimension of the stacked sensor device 100.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method for implanting an intraocular pressure (IOP) sensor device in an eye of a patient, said method comprising:
    positioning an IOP sensor of the IOP sensor device within a vitreous body of the eye by injecting the IOP sensor into the vitreous body to measure the IOP of a vitreous humour, wherein the IOP sensor device resides in a support structure, wherein the IOP sensor is injected by a fluid-filled syringe;
    anchoring the IOP sensor within the vitreous body of the eye with one or more anchoring members of the support structure, the one or more anchoring members being integral parts of the support structure; and
    releasing the IOP sensor from the fluid-filled syringe by pushing the IOP sensor through a distal tip thereof by displacing a fluid within the syringe, wherein displacing the fluid from the syringe comprises retracting the distal tip from the syringe so as to stabilize a position of the IOP sensor within the vitreous body during release from the syringe.

2. The method of claim 1, wherein a sensing diaphragm of the IOP sensor is disposed entirely within the vitreous body for direct measurement of the IOP of the vitreous humour.

3. The method of claim 1, further comprising:
    correlating a sensitivity of the IOP measurement of the vitreous humour to an IOP of the aqueous humour in an anterior chamber of the eye.

4. The method of claim 1, further comprising:
    penetrating partly through a sclera of the eye with an instrument; and
    advancing the IOP sensor into the partly penetrated sclera so as to complete penetration of the sclera with a distal tip of the IOP sensor.

5. The method of claim 1, further comprising:
    penetrating a distal tip of an injector or syringe through a conjunctiva and a sclera of the eye and into the vitreous body, wherein the IOP sensor is injected through the distal tip of the injector or syringe.

6. The method of claim 5 wherein positioning the IOP sensor comprises distally advancing the distal tip of the injector or syringe until a distal facing surface of the injector or syringe abuts against the conjunctiva.

7. The method of claim 5, wherein the distal tip comprises a needle having a gauge of 19 or higher, wherein the IOP sensor comprises a portion of a sensor device having a maximum thickness of about 600 microns or less to facilitate injection through the needle along an insertion axis in-plane with the sensor device.

8. The method of claim 5 further comprising: releasing the IOP sensor from the injector or syringe.

9. The method of claim 5, further comprising:
    positioning the injector or syringe within an ora serrata region of the eye prior to penetrating the distal tip of the injector or syringe so as to avoid any optic structures of a retina of the eye.

10. The method of claim 9, further comprising:
    injecting a fluid into the conjunctiva prior to penetrating the distal tip of the injector or syringe, thereby creating at least a ballooned portion of the conjunctiva in the ora serrata region.

11. The method of claim 10, wherein the fluid comprises an anesthetic such that injecting the fluid into the conjunctiva reduces sensitivity in the eye of the patient prior to penetrating the sclera with the distal tip of the injector or syringe.

12. The method of claim 10, wherein penetrating comprises inserting the distal tip of the injector or syringe through the conjunctiva at the at least ballooned portion, and wherein anchoring comprises deploying the one or more anchoring members along the sclera and covering a proximal end of the device with the conjunctiva after implantation.

13. The method of claim 12, further comprising orienting the distal tip of the injector or syringe substantially perpendicular to the sclera after insertion into the conjunctiva at the at least ballooned portion to facilitate penetration of the sclera and avoid any optic structures of a retina of the eye.

14. The method of claim 7, wherein the IOP sensor includes a MEMs device formed by a wafer process, wherein the sensor device is injected along an insertion axis in-plane with the MEMs device.

15. The method of claim 14, further comprising:
anchoring the IOP sensor within the vitreous body by deploying the one or more anchoring members against the sclera.

16. The method of claim 15, wherein the one or more anchoring members are resiliently biased to extend laterally outward relative to the insertion axis and are constrained within the distal tip toward the insertion axis such that releasing the IOP sensor from the injector or syringe deploys the one or more anchoring members.

17. The method of claim 15, wherein the one or more anchoring members are deployed proximally of the sclera along the insertion axis so as to inhibit movement of the IOP sensor further into the vitreous body by engaging the one or more deployed anchoring members substantially flush with the sclera.

18. The method of claim 15, wherein the one or more anchoring members comprise at least a first and second anchoring member such that anchoring comprises deploying the first anchoring member along the sclera outside of the vitreous body and deploying the second anchoring member along the sclera inside the vitreous body so as to inhibit axial movement of the IOP sensor along the insertion axis after implantation.

19. The method of claim 1, wherein the sensor is injected transverse to a pars plana region in between the ora serrata and limbus of the eye.

20. The method of claim 1, wherein the support structure is an outer casing or housing that extends only partly about the IOP sensor device such that at least a portion of the sensor is exposed.

21. The method of claim 1, wherein positioning comprises advancing a penetrating tip of the support structure through a sclera into the vitreous body, and anchoring comprises engaging the sclera with the one or more anchoring members disposed at a proximal end of the support structure so as to maintain a position of the IOP sensor within the vitreous body.

22. A method for implanting an intraocular pressure (IOP) sensor device in an eye of a patient, said method comprising:
positioning an IOP sensor of the IOP sensor device within a vitreous body of the eye by injecting the IOP sensor into the vitreous body to measure the IOP of a vitreous humour, wherein the IOP sensor device resides in a support structure, wherein the IOP sensor is injected by a fluid-filled syringe;
anchoring the IOP sensor within the vitreous body of the eye with one or more anchoring members of the support structure, the one or more anchoring members being integral parts of the support structure; and
releasing the IOP sensor from the fluid-filled syringe by pushing the IOP sensor through a distal tip thereof by displacing a fluid within the syringe, wherein releasing the IOP sensor comprises retracting the distal tip into a body of the injector or syringe while a distal facing surface of the injector or syringe is abutted against the conjunctiva.

23. The method of claim 22, wherein releasing the IOP sensor comprises maintaining a position of the IOP sensor within the vitreous body using a pusher member during retraction of the distal tip into the body of the injector or syringe.

24. A method for implanting an intraocular pressure (IOP) sensor device in an eye of a patient, said method comprising:
positioning an IOP sensor of the IOP sensor device within a vitreous body of the eye by injecting the IOP sensor into the vitreous body to measure the IOP of a vitreous humour, wherein the IOP sensor device resides in a support structure, wherein the IOP sensor includes a MEMs device formed by a wafer process, wherein the sensor device is injected along an insertion axis in-plane with the MEMs device;
anchoring the IOP sensor within the vitreous body of the eye with one or more anchoring members of the support structure, the one or more anchoring members being integral parts of the support structure;
penetrating a distal tip of an injector or syringe through a conjunctiva and a sclera of the eye and into the vitreous body, wherein the IOP sensor is injected through the distal tip of the injector or syringe, wherein the distal tip comprises a needle having a gauge of 19 or higher, wherein the IOP sensor comprises a portion of a sensor device having a maximum thickness of about 600 microns or less to facilitate injection through the needle along an insertion axis in-plane with the sensor device; and
anchoring the IOP sensor within the vitreous body by deploying the one or more anchoring members against the sclera, wherein the one or more anchoring members and the IOP sensor are defined portions of a MEMs device formed by a wafer process, the one or more anchoring members being proximal of the IOP sensor along the insertion axis such that the IOP sensor resides within the vitreous body while the one or more anchoring members are deployed proximally of the sclera along the insertion axis.

25. The method of claim 24, wherein anchoring comprises engaging the sclera by the one or more anchoring members that are resiliently deflectable in a direction in-plane with a wafer in which the one or more anchoring members are formed.

26. A method for implanting an intraocular pressure (IOP) sensor in an eye of a patient, the method comprising:
positioning an IOP sensor within a vitreous body of the eye by injecting the IOP sensor into the vitreous body to measure the IOP within a vitreous humour of the eye;
penetrating a distal tip of an injector or syringe through a conjunctiva and a sclera of the eye and into the vitreous body, wherein the IOP sensor is injected through the distal tip of the injector or syringe, wherein the distal tip comprises a needle having a gauge of 19 or higher and the IOP sensor comprises a portion of a sensor device having a maximum thickness of about 600 microns or less to facilitate injection through the needle along an insertion axis in-plane with the sensor device, the IOP sensor including a MEMs device formed by a wafer process, wherein the sensor device is injected along an insertion axis in-plane with the MEMs device;
anchoring the IOP sensor within the vitreous body by deploying one or more anchoring members against the sclera, wherein the one or more anchoring members comprise at least a first and second anchoring member such that anchoring comprises deploying the first anchoring member along the sclera outside of the vitreous body and deploying the second anchoring member along the sclera inside the vitreous body so as to inhibit axial movement of the IOP sensor along the insertion axis after implantation; and extracting the IOP sensor by attaching an extraction tool to an extraction feature of the IOP sensor disposed outside the vitreous body, wherein extracting comprises pulling the extraction feature until an anchoring force provided by the at least second anchoring member is overcome.

27. A method for implanting an intraocular pressure (IOP) sensor device in an eye of a patient, said method comprising:
positioning an IOP sensor of the IOP sensor device within a vitreous body of the eye by injecting the IOP sensor into the vitreous body to measure the IOP of a vitreous humour, wherein the IOP sensor device resides in a support structure, wherein the IOP sensor includes a separate reference sensor disposed adjacent the IOP sensor configured for detecting second order effects associated with stress in the sensor device to allow cancellation of the second order effects from the pressure measurement obtained from the IOP sensor; and
anchoring the IOP sensor within the vitreous body of the eye with one or more anchoring members of the support structure, the one or more anchoring members being integral parts of the support structure.

28. The method of claim 27, further comprising:
embedding data, with the implanted IOP sensor device, within the IOP measurement relating to the second order effects detected by the reference sensor.

29. A method for implanting an intraocular pressure (IOP) sensor in an eye of a patient, the method comprising:
positioning an IOP sensor within a vitreous body of the eye by injecting the IOP sensor into the vitreous body to measure the IOP of a vitreous humour, wherein the IOP sensor includes a reference sensor disposed adjacent the IOP sensor configured for detecting one or more second order effects so as to allow cancellation of the second order effects from the pressure measurement obtained from the IOP sensor, wherein the IOP sensor and the reference sensor are of a substantially similar construction having a cavity, except the cavity of the IOP sensor is under vacuum such that the sensing diaphragm is sensitive to changes of pressure such that a signal from the IOP sensor corresponds to changes in pressure and the corresponding cavity of the reference sensor is filled such that a signal obtained from the reference sensor corresponds to the second order effects; and cancelling the second order effects associated with the IOP measurement obtained from the IOP sensor using the signal from the reference sensor.

30. A method of anchoring an implant, the method comprising:
inserting an implantable device through a distal tip of an injector or syringe along an insertion axis into a body tissue or body space within a patient, the device being formed, at least in part, by a wafer process; and
deploying one or more anchoring members of the device so as to extend laterally outward from the insertion axis to inhibit movement of the implanted device within the body tissue or body space, wherein the one more anchoring members comprise a portion of a wafer of the device defined so as to be resiliently deflectable in a direction in-plane with the wafer.

* * * * *